US011839703B2

(12) United States Patent
Lee

(10) Patent No.: US 11,839,703 B2
(45) Date of Patent: Dec. 12, 2023

(54) ATOMIZER STRUCTURE AND ATOMIZER HAVING THE SAME

(71) Applicant: Bloomy Lotus Limited, Central (HK)

(72) Inventor: Leander Lee, New York, NY (US)

(73) Assignee: BLOOMY LOTUS LIMITED, Central (HK)

( * ) Notice: Subject to any disclaimer, the term of this patent is extended or adjusted under 35 U.S.C. 154(b) by 0 days.

(21) Appl. No.: 17/379,561

(22) Filed: Jul. 19, 2021

(65) Prior Publication Data

US 2021/0347554 A1     Nov. 11, 2021

(30) Foreign Application Priority Data

Jun. 25, 2021   (CN) .......................... 202110714252.0

(51) Int. Cl.
*A61L 9/14*  (2006.01)
*B05B 7/24*  (2006.01)
*B05B 7/00*  (2006.01)

(52) U.S. Cl.
CPC .............. *A61L 9/14* (2013.01); *B05B 7/0012* (2013.01); *B05B 7/2408* (2013.01);
(Continued)

(58) Field of Classification Search
CPC ... B05B 7/0012; B05B 7/2408; B05B 7/2416; B05B 7/2424; A61L 2209/134; A61L 9/14
(Continued)

(56) References Cited

U.S. PATENT DOCUMENTS 4,844,072 A * 7/1989 French ...................... A61F 7/02
219/535
5,056,948 A * 10/1991 Puder .................... B05B 3/0472
134/57 R
(Continued)

FOREIGN PATENT DOCUMENTS

CN         2878715 Y      3/2007
CN       103182097 A      7/2013
(Continued)

OTHER PUBLICATIONS

Machine Translation of CN-112108285-A Description, Mar. 2022, Espacenet, 6 Pages (Year: 2022).*
(Continued)

*Primary Examiner* — Tuongminh N Pham
*Assistant Examiner* — Kevin Edward Schwartz
(74) *Attorney, Agent, or Firm* — CANTOR COLBURN LLP

(57) ABSTRACT

The present application provides an atomizer structure and an atomizer having the same. The atomizer structure includes: a spray assembly including a first cavity; a bottle body configured for containing liquid and configured to be connectable to the spray assembly, the bottle body comprises a second cavity; a first connecting member communicating the first cavity and the second cavity and configured for guiding the liquid contained in the second cavity to enter the first cavity, when an air pressure in the first cavity is less than an air pressure in the second cavity; and a second connecting member selectively communicating the first cavity and the second cavity such that a quantity of remaining liquid in the first cavity can enter the second cavity, and configured for preventing liquid in the second cavity from flowing into the first cavity when the atomizer structure is tilted or inverted.

8 Claims, 11 Drawing Sheets

(52) U.S. Cl.
CPC .......... B05B 7/2416 (2013.01); B05B 7/2424 (2013.01); *A61L 2209/134* (2013.01)

(58) Field of Classification Search
USPC ........................................................ 239/338
See application file for complete search history.

(56) References Cited

U.S. PATENT DOCUMENTS

| | | | | |
|---|---|---|---|---|
| 7,066,406 | B2* | 6/2006 | Williams ................ | B05B 15/40 |
| | | | | 239/525 |
| 7,878,418 | B2* | 2/2011 | Sevy .................... | B05B 7/2416 |
| | | | | 128/200.18 |
| 8,919,669 | B2* | 12/2014 | Sandahl ................ | B05B 9/0861 |
| | | | | 239/332 |
| 10,537,903 | B2 | 1/2020 | Sillince | |
| 2017/0036177 | A1* | 2/2017 | Rosener ................. | B05B 15/30 |
| 2017/0072085 | A1* | 3/2017 | Gruenbacher .......... | A61L 9/145 |
| 2019/0299230 | A1* | 10/2019 | Song ..................... | B05B 7/2429 |
| 2022/0088257 | A1* | 3/2022 | Lee ....................... | B05B 7/2424 |

FOREIGN PATENT DOCUMENTS

| | | | | | |
|---|---|---|---|---|---|
| CN | 103182097 | A | * | 7/2013 | ............... A61L 9/14 |
| CN | 203354963 | U | * | 12/2013 | |
| CN | 203916959 | U | | 11/2014 | |
| CN | 108778518 | A | | 11/2018 | |
| CN | 109641226 | A | | 4/2019 | |
| CN | 209061411 | U | | 7/2019 | |
| CN | 110087692 | A | | 8/2019 | |
| CN | 209849121 | U | | 12/2019 | |
| CN | 210906611 | U | | 7/2020 | |
| CN | 210992016 | U | | 7/2020 | |
| CN | 211989239 | U | * | 11/2020 | |
| CN | 112108285 | A | * | 12/2020 | ........... B05B 7/0416 |
| CN | 112108285 | A | | 12/2020 | |
| CN | 212328664 | U | | 1/2021 | |
| CN | 112403705 | A | | 2/2021 | |
| CN | 213158102 | U | | 5/2021 | |
| CN | 213216675 | U | * | 5/2021 | |

OTHER PUBLICATIONS

Machine Translation of CN-103182097-A Description, Mar. 2022, Espacenet, 4 Pages (Year: 2022).*
Machine Translation of CN-213216675-U Description, Espacenet, Jul. 2022, 4 Pages (Year: 2022).*
Machine Translation of CN-211989239-U Description, Espacenet, Jul. 2022, 5 Pages (Year: 2022).*
Machine Translation of CN-203354963-U Description, Jan. 2023, Espacenet, 6 Pages (Year: 2023).*
Search Report for Chinese Application No. 2021107142520; dated Apr. 25, 2022; 2 Pages.

* cited by examiner

ATOMIZER STRUCTURE AND ATOMIZER HAVING THE SAME

CROSS REFERENCE TO RELATED APPLICATION

The present application claims priority of Chinese Patent Application Serial No. 202110714252.0, filed on Jun. 25, 2021, the entire content of which is incorporated herein by reference.

TECHNICAL FIELD

The present application relates to the field of atomizers, and more particularly to an atomizer structure and an atomizer having the same.

BACKGROUND

In daily life, essential oils or similar liquids are often used to improve the surrounding environment or to perform medical treatment, such as sterilization, disinfection or changing environmental odor, etc. When using the essential oils or the similar liquids, an atomizer is often used to atomize the essential oils or the similar liquids for facilitating diffusion of the essential oils into the environment.

SUMMARY

An object of the present application is to provide an atomizer, in order to solve the problem that essential oils or similar liquids contained in the bottle easily leak out when the existing atomizer structure is tilted or inverted.

In a first aspect of the present application, an atomizer structure is provided, which includes:

a spray assembly, including a first cavity;

a bottle body, configured for containing liquid and configured to be connectable to the spray assembly, wherein the bottle body comprises a second cavity;

a first connecting member, communicating the first cavity and the second cavity and configured for guiding the liquid contained in the second cavity entering the first cavity, when an air pressure in the first cavity is less than an air pressure in the second cavity; and a second connecting member, selectively communicating the first cavity and the second cavity such that remaining liquid in the first cavity entering the second cavity, and configured for preventing the liquid in the second cavity from flowing into the first cavity when the atomizer structure is tilted or inverted.

In an alternative but non-limiting embodiment of the present application, the first connecting member is a liquid suction tube connected between the first cavity and the second cavity; and the second connecting member is a liquid return tube, connected between the first cavity and the second cavity;

and the liquid suction tube and the liquid return tube are configured for keeping the air pressure of the first cavity equal to the air pressure of the second cavity when the atomizer structure is not in use.

In an alternative but non-limiting embodiment of the present application, the liquid suction tube comprises a first end and a second end, the first end extending into the first cavity, and the second end can extend into the second cavity; and the liquid return tube comprises a third end and a fourth end, an opening of the third end being located at a bottom of the first cavity, and the fourth end can extend into the second cavity;

and the second end and the fourth end are both connected to a holder.

In an alternative but non-limiting embodiment of the present application, the first cavity comprises a cavity portion and a liquid return portion located below the cavity portion, the liquid return portion being in a shape of a funnel, and the opening of the third end is located at a lowermost end of the liquid return portion.

In an alternative but non-limiting embodiment of the present application, the spray assembly further includes a plurality of pressure relief holes communicating with the first cavity, and the pressure relief holes are configured to pass through the pressure relief hole allowing the first cavity to communicate with an atmosphere outside the first cavity.

In an alternative but non-limiting embodiment of the present application, shapes of the pressure relief holes are configured to prevent the first cavity from being separated with the atmosphere outside the first cavity when the pressure relief holes are blocked by a plate-shaped member.

In an alternative but non-limiting embodiment of the present application, the first connecting member is a liquid suction tube connected between the first cavity and the second cavity; and the second connecting member is a duckbill valve, connected between the first cavity and the second cavity;

and the duckbill valve is configured to prevent the liquid contained in the second cavity from flowing into the first cavity when the air pressure in the first cavity and the air pressure in the second cavity are balanced.

In an alternative but non-limiting embodiment of the present application, the first connecting member is a liquid suction tube connected between the first cavity and the second cavity; and the second connecting member is a one-way valve, connected between the first cavity and the second cavity;

and the one-way valve is configured to prevent the liquid contained in the second cavity from flowing into the first cavity when the air pressure in the first cavity and the air pressure in the second cavity are balanced.

In an alternative but non-limiting embodiment of the present application, the first connecting member is a liquid suction tube connected between the first cavity and the second cavity, the liquid suction tube is provided with a duckbill valve configured to prevent the liquid contained in the second cavity from flowing into the first cavity when the air pressure in the first cavity and the air pressure in the second cavity are balanced; and the second connecting member is a liquid return tube, connected between the first cavity and the second cavity;

and the liquid suction tube and the liquid return tube are configured for keeping the air pressure of the first cavity equal to the air pressure of the second cavity when the atomizer structure is not in use.

In an alternative but non-limiting embodiment of the present application, the first connecting member is a liquid suction tube connected between the first cavity and the second cavity, the liquid suction tube is provided with a one-way valve configured to prevent the liquid contained in the second cavity from flowing into the first cavity when the air pressure in the first cavity and the air pressure in the second cavity are balanced; and the second connecting member is a liquid return tube, connected between the first cavity and the second cavity;

and the liquid suction tube and the liquid return tube are configured for keeping the air pressure of the first cavity equal to the air pressure of the second cavity when the atomizer structure is not in use.

In an alternative but non-limiting embodiment of the present application, the first connecting member is a liquid suction tube connected between the first cavity and the second cavity, the liquid suction tube is provided with a duckbill valve configured to prevent the liquid contained in the second cavity from flowing into the first cavity when the air pressure in the first cavity and the air pressure in the second cavity are balanced; and the second connecting member is a one-way valve, connected between the first cavity and the second cavity;

and the one-way valve is configured to prevent the liquid contained in the second cavity from flowing into the first cavity when the air pressure in the first cavity and the air pressure in the second cavity are balanced.

In an alternative but non-limiting embodiment of the present application, the first connecting member is a liquid suction tube connected between the first cavity and the second cavity, the liquid suction tube is provided with a one-way valve configured to prevent the liquid contained in the second cavity from flowing into the first cavity when the air pressure in the first cavity and the air pressure in the second cavity are balanced; and the second connecting member is a duckbill valve, connected between the first cavity and the second cavity;

and the duckbill valve is configured to prevent the liquid contained in the second cavity from flowing into the first cavity when the air pressure in the first cavity and the air pressure in the second cavity are balanced.

In an alternative but non-limiting embodiment of the present application, the first connecting member is a liquid suction tube connected between the first cavity and the second cavity, the liquid suction tube is provided with a first one-way valve configured to prevent the liquid contained in the second cavity from flowing into the first cavity when the air pressure in the first cavity and the air pressure in the second cavity are balanced; and the second connecting member is a second one-way valve, connected between the first cavity and the second cavity;

and the second one-way valve is configured to prevent the liquid contained in the second cavity from flowing into the first cavity when the air pressure in the first cavity and the air pressure in the second cavity are balanced.

In an alternative but non-limiting embodiment of the present application, a sealing member is further disposed between the first cavity and the second cavity, through which the first connecting member and the second connecting member passing through.

In an alternative but non-limiting embodiment of the present application, an upper end of the first connecting member is located in the first cavity, and a liquid nozzle is further provided at the upper end, and the liquid nozzle is in a cone shape.

In an alternative but non-limiting embodiment of the present application, the atomizer structure further includes a gas supplying assembly, the gas supplying assembly including an air pump and an air tube connected to an outlet of the air pump, the other end of the air tube is connected with a gas nozzle, and a front end of the gas nozzle extends into the first cavity such that an opening of the gas nozzle faces an opening of the liquid nozzle.

In an alternative but non-limiting embodiment of the present application, an angle of less than 90 degrees is formed between an outlet axis of the gas nozzle and an outlet axis of the liquid nozzle.

In a second aspect of the present application, an atomizer is provided, which includes the atomizer structure abovementioned and a power supply assembly configured to supply power to the atomizer structure, and a controller electrically connected to the power supply assembly, the controller including a tilting switch configured to disconnect the power supply assembly from supplying power to the atomizer structure when the atomizer structure is tilted or inverted.

In the present application, the atomizer structure is provided with the first connecting member and the second connecting member, and in a non-use state, the first cavity and the second cavity are maintained air pressure balance due that the communication of the first connecting member and the second connecting member, and the second connecting member is configured to prevent the liquid contained in the second cavity from flowing into the first cavity when the atomizer structure is tilted or inverted, that is, after the atomizer structure is tilted or during the atomizer structure is tilting, since there is no external air pressure interference, the air pressure in the first cavity and the second cavity will not change, thereby the liquid contained in the bottle body will not enter the first cavity through the first connecting member, in addition, due to the arrangement of the second connecting member, the liquid contained in the bottle body will not enter the first cavity through the second connecting member; therefore, when the atomizer structure is not in use, the problem that the liquid contained in the bottle body leaks after being knocked down due to accidental touch and other reasons can be avoided.

In the present application, with the arrangement of the atomizer structure, when the atomizer structure is not in use, the problem that the liquid contained in the bottle body leaks after being knocked down due to accidental touch and other reasons can be avoided. In addition, with the arrangement of the tilting switch, when the atomizer in use is knocked down, the tilting switch stops the power supply assembly to power the atomizer structure, and the atomizer structure enters the non-use state, therefore, when the atomizer is in use, the problem that the liquid contained in the bottle body leaks after being knocked down due to accidental touch and other reasons can be avoided.

BRIEF DESCRIPTION OF THE DRAWINGS

The accompanying drawings and figures illustrate a number of exemplary embodiments and are part of the specification. Together with the present description, these drawings demonstrate and explain various principles of this disclosure. A further understanding of the nature and advantages of the present invention may be realized by reference to the following drawings. In the appended figures, similar components or features may have the same reference label.

Figure 1:
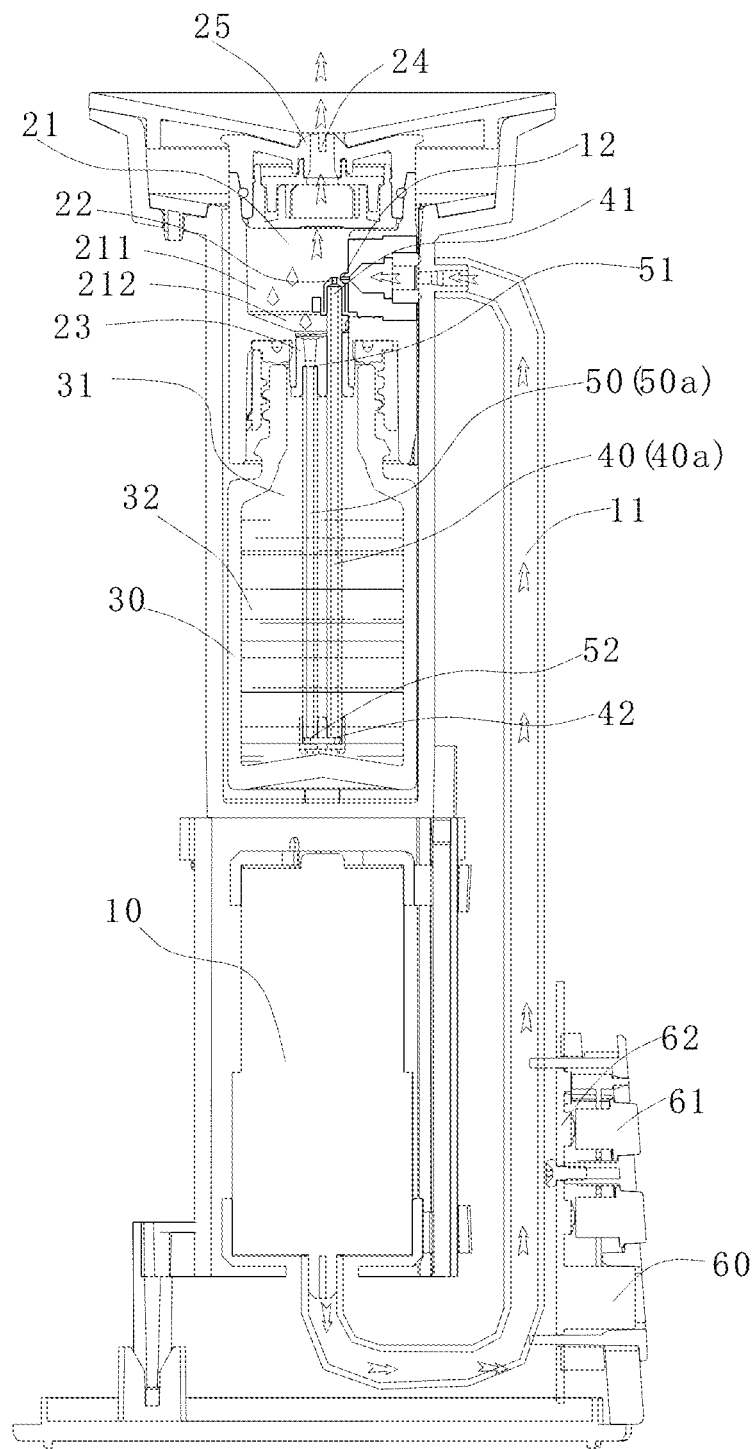
FIG. 1 is a cross-sectional view of an atomizer provided by a first embodiment of the present application.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

Traditional atomizers usually spray high-speed airflow through an air pump device to extract liquid from the bottle body. In the present application, it is preferable to extract essential oils from the essential oil bottle and transfer the essential oils from the atomizer to the surrounding atmosphere. In this process, the gas enters the atomizing cavity (hereinafter referred to as the "first cavity") through the gas nozzle, so that a negative pressure is formed above the outlet of the liquid nozzle connected to the upper end of the first connecting member (hereinafter referred to as the "liquid suction tube"), which makes the liquid contained in the bottle body enter the first cavity through the liquid suction tube; affected by the gas sprayed by the gas nozzle, the liquid is atomized in the first cavity to form a mixed gas with the gas, then the mixed gas is discharged into the surrounding atmosphere through the mist outlet.

In the above atomizing process, a specific filter or similar structure can also be provided in the first cavity, so that the larger liquid droplets in the mixed gas flow back to the bottom of the first cavity; in the traditional atomizers, the bottom of the first cavity is usually provided with a channel communicating with the bottle body, so as to facilitate the flow of the returned liquid into the bottle body. However, this design will cause the liquid contained in the bottle body to flow out of the atomizer or machine when the atomizer or machine is tilted to the side, inverted and/or shaken; the traditional atomizer structure usually contains essential oils in the bottle body, and when the atomizer structure or the machine is tilted to the side, inverted and/or shaken, the essential oils will be wasted.

It is noted that when a component is referred to as being "fixed to," "installed on," "arranged on" or "disposed on" another component, it can be directly or indirectly fixed on another component. When a component is referred to as being "connected to" another component, it can be directly or indirectly connected to the other component.

In addition, the terms "first" and "second" are for illustrative purposes only and should not be construed as indicating or implying a relative importance or indicating the quantity of technical features. Therefore, a feature that is qualified as "first" and "second" may expressly or implicitly include one or more of such a feature. In the description of the present invention, "multiple" means two or more, unless otherwise specifically defined.

Unless specified otherwise, it should be understood that, "length", "width", "upper", "lower", "front", "back", "left" and "right", "vertical", "horizontal", "top", "bottom", "inside", "outside" and other terms indicating the orientation or positional relationship are used to refer to orientation or positional relationship shown in the drawings, only for the purpose of facilitating and simplifying the description of the invention, instead of indicating or implying that the indicated device or component must have a specific orientation and constructed and operated in a particular orientation, and therefore cannot be construed as limiting.

In the description of the present invention, it should be noted that the terms "install," "connected," and "connect" should be interpreted broadly unless specifically defined or limited otherwise. For example, the components may be fixedly connected or they may be detachable connected, or integral connected. The connection can be mechanical or electrical. The connection can be direct or indirect (connected through an intermediary). It can also be the internal communication of two components or the interaction between two components. Those of ordinary skill in the art can understand the specific meanings of the above terms in the present disclosure according to specific circumstances.

Embodiment 1

Figure 2:
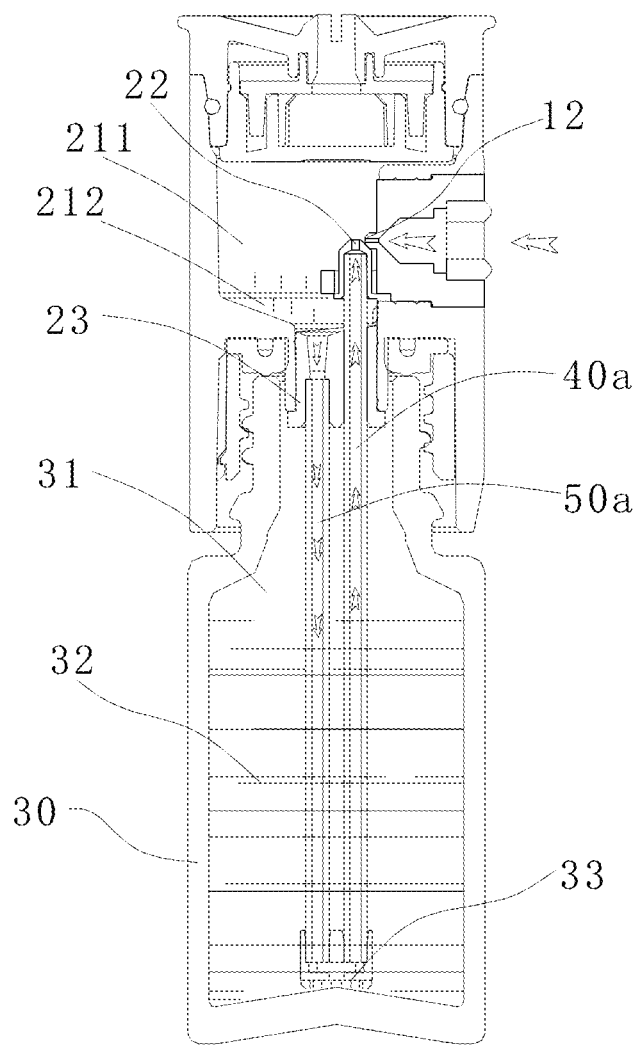
FIG. 2 is a cross-sectional view of an atomizer structure provided by a first embodiment of the present application, the atomizer structure is in use state.
Figure 3:
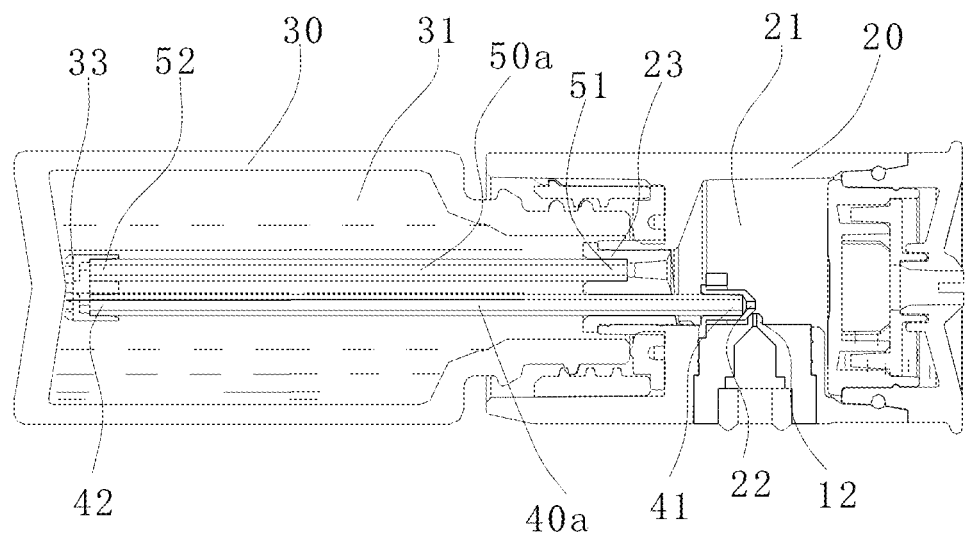
FIG. 3 is a cross-sectional view of an atomizer structure provided by a first embodiment of the present application, the atomizer structure is not in a non-use state of horizontally tilted.
Figure 4:
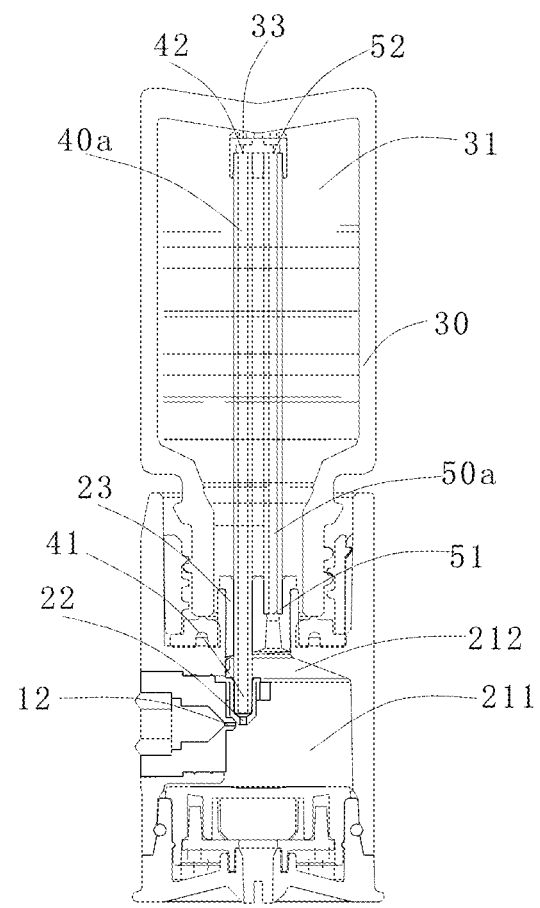
FIG. 4 is a cross-sectional view of an atomizer structure provided by a first embodiment of the present application, the atomizer structure is not in a non-use state of vertically inverted.

FIGS. 1-4 show the first embodiment of the atomizer structure and the atomizer having the same provided by the present application. FIG. 1 shows a structural view of the atomizer provided in the first embodiment of the present application in use state. FIG. 2 shows a cross-sectional view of the atomizer structure provided by the first embodiment of the present application, among them, the atomizer structure is in use state, the gas is blown into the atomizing cavity through the gas nozzle 12, and atomizing the liquid 32 sucked from the bottle body 30 through the liquid nozzle 22, and then the atomized liquid is diffused out through the mist outlet 25. FIG. 3 shows a cross-sectional view of the atomizer structure provided in the first embodiment of the present application, among them, the atomizer structure is not in use state and is in a horizontally tilted state, and the air pressures in the atomizing cavity and the bottle body 30 are balanced, the liquid in the atomizing cavity and the bottle body 30 cannot enter the each other. FIG. 4 shows a cross-sectional view of the atomizer structure provided in the first embodiment of the present application, among them, the atomizer structure is not in use state and is in a vertically inverted state, and the air pressures in the atomizing cavity and the bottle body 30 are balanced, the liquid in the bottle body 30 cannot enter the atomizing cavity due to inversion.

In the embodiment, the atomizer structure includes a gas supplying assembly, which includes an air pump 10, an air tube 11 connected to the air pump 10, and a gas nozzle 12 connected to the end of the air tube 11. The atomizer structure also includes a spray assembly 20 and a bottle body 30 connected to the spray assembly 20. The bottle body 30 is configured to contain the liquid 32 and is configured to be connectable to the spray assembly 20, and the bottle body 30 includes a second cavity 31; the spray assembly 20 includes a first cavity 21 for atomizing the liquid 32, a plurality of mist outlet holes 25 communicating with the first cavity 21, and a liquid nozzle 22 arranged in the first cavity 21. In the embodiment, the outlet end of the gas nozzle 12 is located in the first cavity 21 such that the gas outlet of the gas nozzle 12 faces the liquid outlet of the liquid nozzle 22; that is, the gas blown from the gas pump 10 through the air tube 11 blows directly to the liquid nozzle 22 and enters the first cavity 21.

In the embodiment, the gas outlet of the gas nozzle 12 is located adjacent to the liquid outlet of the liquid nozzle 22, and is configured to guide the airflow leaving the gas pump 10 to the liquid outlet of the liquid nozzle 22, therefore, when the air pump 10 provides a high-pressure airflow and ejects the airflow from the gas nozzle 12, a negative pressure is formed at the upper end of the liquid nozzle 22 to extract liquid 32 (eg, essential oil) from the bottle body 30 through the liquid nozzle 22. Then, the extracted essential oil droplets can be atomized by the high-speed airflow from the gas nozzle 12 to form a mixed airflow containing essential oil droplets; finally, a suitable atomized airflow is diffused into the surrounding atmosphere.

In a preferred embodiment of the present application, the outlet of the gas outlet of the gas nozzle 12 axially points to the top of the upper end of the side wall of the liquid nozzle 22. Further preferably, the outlet axis of the gas nozzle 12 and the outlet axis of the liquid nozzle 22 form an angle of less than 90 degrees. Furthermore, when the airflow is ejected from the gas outlet of the gas nozzle 12, the airflow can cover the upper end of the liquid nozzle 22 to form a better negative pressure at the upper end of the liquid nozzle 22 (for example, due to the Bernoulli effect), which can facilitate extracting liquid 32, such as essential oil, from the bottle body 30. Therefore, the top of the side wall of the liquid nozzle 22 can change the direction of the airflow ejected from the gas nozzle 12 (for example, by blocking at least some of the airflow), thereby improving the atomization of the essential oil droplets sucked from the liquid nozzle 22.

In the application, the gas supplying assembly is preferably arranged below the bottle body 30, and the air tube 11 is arranged on the side of the atomizer structure; the bottle body 30 is preferably detachably connected below the spray assembly 20, where the detachable connection is preferably a threaded connection.

In the embodiment, the atomizer structure further includes a first connecting member 40 that communicates with the first cavity 21 and the second cavity 31 and is configured to allow the liquid 32 contained in the second cavity 31 entering the first cavity 21, when the air pressure of the first cavity 21 is lower than the air pressure of the second cavity 31. The first connecting member 40 communicates the first cavity 21 and the second cavity 31 in a natural state, that is, in a normal use state, and the liquid 32 in the bottle body 30 can enter the first cavity 21 through the first connecting member 40 and then being atomized.

Optionally, the first connecting member 40 is preferably a liquid suction tube 40a connected between the first cavity 21 and the second cavity 31. The liquid suction tube 40a includes a first end 41 located at the upper part and a second end 42 opposite to the first end 41, and the first end 41 extends into the first cavity 21, such that in a normal state, the horizontal height of the first end 41 is higher that the horizontal height of the bottom surface of the first cavity 21; that is, the first end 41 extends into the inside of the first cavity 21. The second end 42 can extend into the second cavity 31. Here, the second end 42 is preferably approximately close to the bottom surface inside the bottle body 30, and ensures that there is a gap between the second end 42 and the bottom surface inside of the bottle body 30 for the liquid 32 to circulate.

In the embodiment, the atomizer structure further includes a second connecting member 50, which replaces the liquid return channel in the traditional atomizer structure; that is, under normal use state, the liquid 32 at the bottom of the first cavity 21 can flow back into the bottle body 30 through the second connecting member 50. However, under abnormal use states, that is, when tilted to the side, inverted, and/or shaken as described above, the second connecting member 50 is configured to prevent liquid 32 contained in the second cavity 31 from flowing into the first cavity 21 when the container structure is tilted to the side, inverted, and/or shaken, when the bottle body 30 is connected to the spray assembly 20. Thereby, it is prevented that the liquid 32 in the bottle body 30 flows out of the atomizer structure in the abnormal use states, which causes the waste of the liquid 32 (for example, essential oil).

Optionally, the second connecting member 50 is preferably a liquid return tube 50a connected between the first cavity 21 and the second cavity 31. In the embodiment, the number of the liquid return tube 50a is at least one. The liquid return tube 50a includes a third end 51 located at the upper part and a fourth end 52 opposite to the third end 51. In the embodiment, in the normal structure of the atomizer, the horizontal height of the third end 51 is smaller than that of the first end 41.

In an alternative embodiment, the opening of the third end 51 is located at the bottom of the first cavity 21; here, the opening of the third end 51 may be aligned with the bottom of the first cavity 21, or the horizontal height of the opening of the third end 51 is lower than the horizontal height of the bottom of the first cavity 21.

In the embodiment, the fourth end 52 can extend into the second cavity 31. Here, the length of the liquid return tube 50*a* extending into the second cavity 31 is preferably equal to that of the liquid suction tube 40*a*; that is, the fourth end 52 is preferably approximately close to the bottom surface of the bottle body 30, and it is ensured that there is a gap between the fourth end 52 and the bottom surface inside of the bottle body 30 for the liquid 32 to circulate.

In an optional embodiment of the present application, the second end 42 and the fourth end 52 are also connected to a holder 33, so that damage to the ends of the liquid suction tube 40*a* and the liquid return tube 50*a* can be avoided.

In an optional embodiment of the present application, the tube diameters of the liquid suction tube 40*a* and the liquid return tube 50*a* are preferably in the range of 0.1-5 mm; this can better maintain the air pressure between the first cavity 21 and the second cavity 31 is balanced, when the atomizer structure is not in use, and even when the atomizer structure is in a tilted or inverted state, the liquid 32 in the second cavity 31 will not pass through the liquid suction tube 40*a* and/or the liquid return tube 50*a* flows into the first cavity 21.

In an optional embodiment of the present application, the liquid nozzle 22 of the atomizer structure is connected to the first end 41 of the liquid suction tube 40*a*, and the liquid nozzle 22 is in a cone shape, and the aperture of the conical outlet finally determines the diameter of the first end 41 of the liquid suction tube 40*a* in the first cavity 21.

In an optional embodiment of the present application, the atomizer structure preferably further includes a sealing member 23 connected below the first cavity 21, and the liquid suction tube 40*a* and the liquid return tube 50*a* can pass through the sealing member 23. In the embodiment, the sealing member 23 is provided with a plurality of holes communicating with the bottom of the first cavity 21, and the liquid suction tube 40*a* and the liquid return tube 50*a* can pass through the sealing member 23 through the holes. Alternatively, the sealing member 23 is provided with a plurality of holes with different diameters communicating with the bottom of the first cavity 21, and these holes allow the liquid suction tube 40*a* to pass through the sealing member 23, and the hole correspond to the liquid return tube 50*a* is a stepped hole, which makes the third end 51 of the liquid return tube 50*a* connected inside of the sealing member 23, but the end of the third end 51 does not enter the first cavity 21.

In an optional embodiment of the present application, the second end 42 and the fourth end 52 are both connected to a holder 33, and the second end 42 and the fourth end 52 are both connected in the holder 33, and the holder 33 is additionally provided with through holes that allows the liquid suction tube 40*a* and the liquid return tube 50*a* to communicate with the second cavity 31, and the hole diameter of the through hole may be smaller than the hole diameter of the liquid suction tube 40*a* and the liquid return tube 50*a*; this design can maintain the air pressure balance between the first cavity 21 and the second cavity 31 when the atomizer structure is not in use, this design can maintain the air pressure balance between the first cavity 21 and the second cavity 31 when the atomizer structure is not in use, by maintaining the diameters of the through holes, the conical outlet of the liquid nozzle 22, and the hole in the sealing member 23; the air pressure balance can also be achieved.

In an optional embodiment of the present application, the first cavity 21 includes a cavity portion 211 and a liquid return portion 212 located below the cavity portion 211, the liquid return portion 212 is in the shape of a funnel, and the opening of the third end 51 is located at the lowermost end of the liquid return portion 212. This design can better strengthen the backflow of the liquid 32.

In an optional embodiment of the present application, the spray assembly 20 further includes a plurality of pressure relief holes 24 communicating with the first cavity 21. In the embodiment, the pressure relief holes 24 are used to maintain the pressure balance between the first cavity 21 and the atmosphere outside the atomizer structure when the atomizer structure is not in use, so as to further maintain the air pressure balance between the first cavity 21 and the second cavity 31. Therefore, if the pressure relief holes 24 are accidentally touched and closed, the air pressure in the first cavity 21 will decrease due to the air pump 10 and the air tube 11, and the liquid 32 in the second cavity 31 will pass through the liquid suction tube 40*a* enters the first cavity 21. Therefore, the number and positions of the pressure relief holes 24 of the present application are set such that they cannot be blocked and sealed by a flat plate structure. For example, the outlets of the multiple pressure relief holes 24 are not in the same plane, or other achievable types.

Embodiment 2

Figure 5:
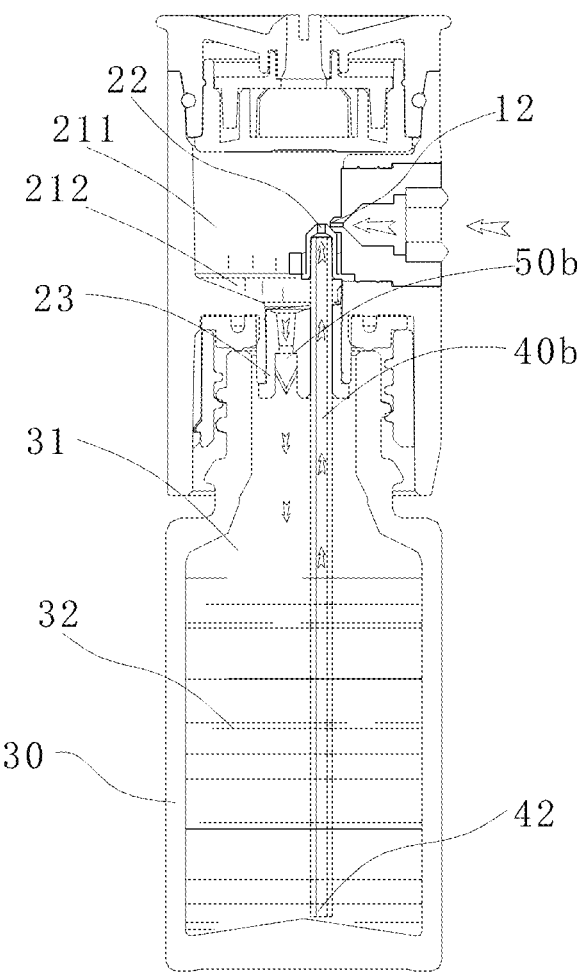
FIG. 5 is a cross-sectional view of an atomizer structure provided by a second embodiment of the present application, the atomizer structure is in use state.
Figure 6:
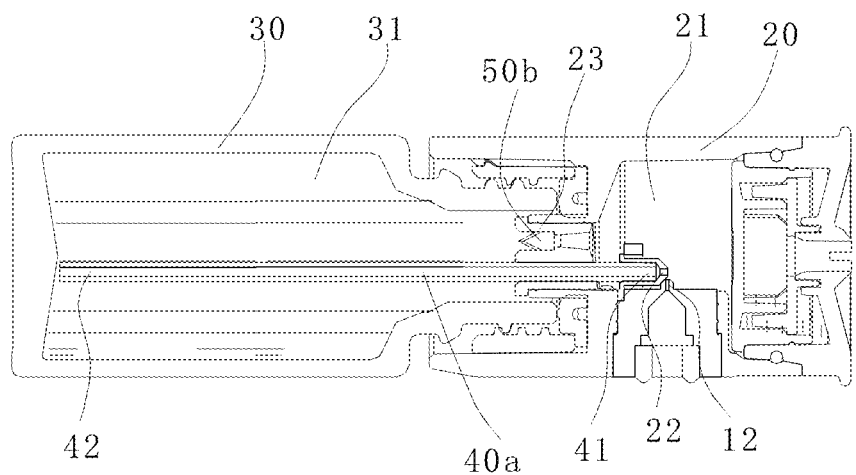
FIG. 6 is a cross-sectional view of an atomizer structure provided by a second embodiment of the present application, the atomizer structure is not in a non-use state of horizontally tilted.
Figure 7:
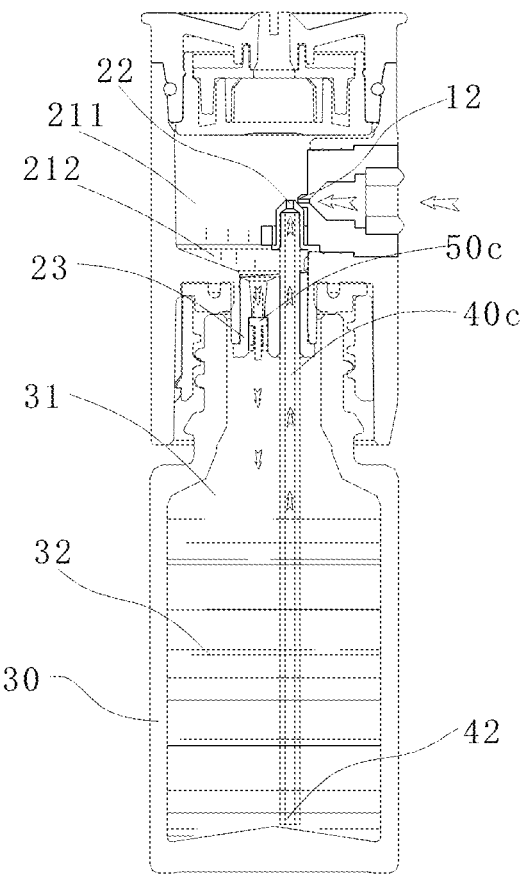
FIG. 7 is a cross-sectional view of an atomizer structure provided by a third embodiment of the present application, the atomizer structure is in use state.
Figure 8:
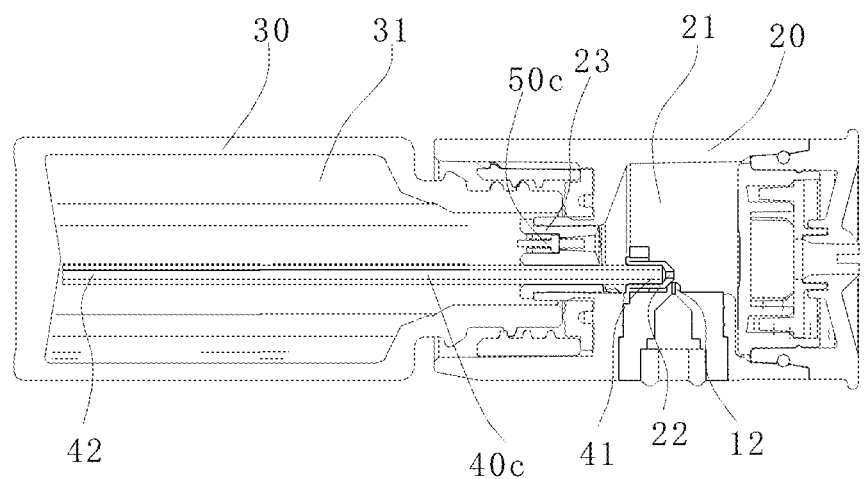
FIG. 8 is a cross-sectional view of an atomizer structure provided by a third embodiment of the present application, the atomizer structure is not in a non-use state of horizontally tilted.

FIGS. 5 and 6 show the second embodiment of the atomizer structure and the atomizer having the same provided by the present application. FIGS. 5 and 6 refer to the similar structural state descriptions in the first embodiment.

In the embodiment, the atomizer structure includes a gas supplying assembly, which includes an air pump 10, an air tube 11 connected to the air pump 10, and a gas nozzle 12 connected to the end of the air tube 11. The atomizer structure also includes a spray assembly 20 and a bottle body 30 connected to the spray assembly 20. The bottle body 30 is configured to contain the liquid 32 and is configured to be connectable to the spray assembly 20, and the bottle body 30 includes a second cavity 31; the spray assembly 20 includes a first cavity 21 for atomizing the liquid 32, a plurality of mist outlet holes 25 communicating with the first cavity 21, and a liquid nozzle 22 arranged in the first cavity 21. In the embodiment, the outlet end of the gas nozzle 12 is located in the first cavity 21 such that the gas outlet of the gas nozzle 12 faces the liquid outlet of the liquid nozzle 22; that is, the gas blown from the gas pump 10 through the air tube 11 blows directly to the liquid nozzle 22 and enters the first cavity 21.

In the embodiment, the gas outlet of the gas nozzle 12 is located adjacent to the liquid outlet of the liquid nozzle 22, and is configured to guide the airflow leaving the gas pump 10 to the liquid outlet of the liquid nozzle 22, therefore, when the air pump 10 provides a high-pressure airflow and ejects the airflow from the gas nozzle 12, a negative pressure is formed at the upper end of the liquid nozzle 22 to extract liquid 32 (eg, essential oil) from the bottle body 30 through the liquid nozzle 22. Then, the extracted essential oil droplets can be atomized by the high-speed airflow from the gas nozzle 12 to form a mixed airflow containing essential oil droplets; finally, a suitable atomized airflow is diffused into the surrounding atmosphere.

In a preferred embodiment of the present application, the outlet of the gas outlet of the gas nozzle 12 axially points to the top of the upper end of the side wall of the liquid nozzle 22. Further preferably, the outlet axis of the gas nozzle 12 and the outlet axis of the liquid nozzle 22 form an angle of less than 90 degrees. Furthermore, when the airflow is ejected from the gas outlet of the gas nozzle 12, the airflow can cover the upper end of the liquid nozzle 22 to form a better negative pressure at the upper end of the liquid nozzle 22 (for example, due to the Bernoulli effect), which can facilitate extracting liquid 32, such as essential oil, from the bottle body 30. Therefore, the top of the side wall of the liquid nozzle 22 can change the direction of the airflow ejected from the gas nozzle 12 (for example, by blocking at least some of the airflow), thereby improving the atomization of the essential oil droplets sucked from the liquid nozzle 22.

In the embodiment, the atomizer structure further includes a first connecting member 40 that communicates with the first cavity 21 and the second cavity 31 and is configured to allow the liquid 32 contained in the second cavity 31 entering the first cavity 21, when the air pressure of the first cavity 21 is lower than the air pressure of the second cavity 31. The first connecting member 40 communicates the first cavity 21 and the second cavity 31 in a natural state, that is, in a normal use state, and the liquid 32 in the bottle body 30 can enter the first cavity 21 through the first connecting member 40 and then being atomized.

Optionally, the first connecting member 40 is preferably a liquid suction tube 40*b* connected between the first cavity 21 and the second cavity 31. The liquid suction tube 40*b* includes a first end 41 located at the upper part and a second end 42 opposite to the first end 41, and the first end 41 extends into the first cavity 21, such that in a normal state, the horizontal height of the first end 41 is higher that the horizontal height of the bottom surface of the first cavity 21; that is, the first end 41 extends into the inside of the first cavity 21. The second end 42 can extend into the second cavity 31. Here, the second end 42 is preferably approximately close to the bottom surface inside the bottle body 30, and ensures that there is a gap between the second end 42 and the bottom surface inside of the bottle body 30 for the liquid 32 to circulate.

In the embodiment, the atomizer structure further includes a second connecting member 50, which replaces the liquid return channel in the traditional atomizer structure; that is, under normal use state, the liquid 32 at the bottom of the first cavity 21 can flow back into the bottle body 30 through the second connecting member 50. However, under abnormal use states, that is, when tilted to the side, inverted, and/or shaken as described above, the second connecting member 50 is configured to prevent liquid 32 contained in the second cavity 31 from flowing into the first cavity 21 when the container structure is tilted to the side, inverted, and/or shaken, when the bottle body 30 is connected to the spray assembly 20. Thereby, it is prevented that the liquid 32 in the bottle body 30 flows out of the atomizer structure in the abnormal use states, which causes the waste of the liquid 32 (for example, essential oil).

Optionally, the second connecting member 50 is preferably a duckbill valve 50*b*. The duckbill valve 50*b* can only flow in one direction, that is, when the air pressure of the first cavity 21 is greater than that of the second cavity 31, the duckbill valve 50*b* communicates the first cavity 21 and the second cavity 31; and when the air pressure of the first cavity 21 is less than or equal to the pressure of the second cavity 31, the duckbill valve 50*b* blocks the communication between the first cavity 21 and the second cavity 31.

Embodiment 3

FIGS. 7 and 8 show the third embodiment of the atomizer structure and the atomizer having the same provided by the present application. FIGS. 7 and 8 refer to the similar structural state descriptions in the first embodiment.

In the embodiment, the atomizer structure includes a gas supplying assembly, which includes an air pump 10, an air tube 11 connected to the air pump 10, and a gas nozzle 12 connected to the end of the air tube 11. The atomizer structure also includes a spray assembly 20 and a bottle body 30 connected to the spray assembly 20. The bottle body 30 is configured to contain the liquid 32 and is configured to be connectable to the spray assembly 20, and the bottle body 30 includes a second cavity 31; the spray assembly 20 includes a first cavity 21 for atomizing the liquid 32, a plurality of mist outlet holes 25 communicating with the first cavity 21, and a liquid nozzle 22 arranged in the first cavity 21. In the embodiment, the outlet end of the gas nozzle 12 is located in the first cavity 21 such that the gas outlet of the gas nozzle 12 faces the liquid outlet of the liquid nozzle 22; that is, the gas blown from the gas pump 10 through the air tube 11 blows directly to the liquid nozzle 22 and enters the first cavity 21.

In the embodiment, the gas outlet of the gas nozzle 12 is located adjacent to the liquid outlet of the liquid nozzle 22, and is configured to guide the airflow leaving the gas pump 10 to the liquid outlet of the liquid nozzle 22, therefore, when the air pump 10 provides a high-pressure airflow and ejects the airflow from the gas nozzle 12, a negative pressure is formed at the upper end of the liquid nozzle 22 to extract liquid 32 (eg, essential oil) from the bottle body 30 through the liquid nozzle 22. Then, the extracted essential oil droplets can be atomized by the high-speed airflow from the gas nozzle 12 to form a mixed airflow containing essential oil droplets; finally, a suitable atomized airflow is diffused into the surrounding atmosphere.

In a preferred embodiment of the present application, the outlet of the gas outlet of the gas nozzle 12 axially points to the top of the upper end of the side wall of the liquid nozzle 22. Further preferably, the outlet axis of the gas nozzle 12 and the outlet axis of the liquid nozzle 22 form an angle of less than 90 degrees. Furthermore, when the airflow is ejected from the gas outlet of the gas nozzle 12, the airflow can cover the upper end of the liquid nozzle 22 to form a better negative pressure at the upper end of the liquid nozzle 22 (for example, due to the Bernoulli effect), which can facilitate extracting liquid 32, such as essential oil, from the bottle body 30. Therefore, the top of the side wall of the liquid nozzle 22 can change the direction of the airflow ejected from the gas nozzle 12 (for example, by blocking at least some of the airflow), thereby improving the atomization of the essential oil droplets sucked from the liquid nozzle 22.

In the embodiment, the atomizer structure further includes a first connecting member 40 that communicates with the first cavity 21 and the second cavity 31 and is configured to allow the liquid 32 contained in the second cavity 31 entering the first cavity 21, when the air pressure of the first cavity 21 is lower than the air pressure of the second cavity 31. The first connecting member 40 communicates the first cavity 21 and the second cavity 31 in a natural state, that is, in a normal use state, and the liquid 32 in the bottle body 30 can enter the first cavity 21 through the first connecting member 40 and then being atomized.

Optionally, the first connecting member 40 is preferably a liquid suction tube 40c connected between the first cavity 21 and the second cavity 31. The liquid suction tube 40c includes a first end 41 located at the upper part and a second end 42 opposite to the first end 41, and the first end 41 extends into the first cavity 21, such that in a normal state, the horizontal height of the first end 41 is higher that the horizontal height of the bottom surface of the first cavity 21; that is, the first end 41 extends into the inside of the first cavity 21. The second end 42 can extend into the second cavity 31. Here, the second end 42 is preferably approximately close to the bottom surface inside the bottle body 30, and ensures that there is a gap between the second end 42 and the bottom surface inside of the bottle body 30 for the liquid 32 to circulate.

In the embodiment, the atomizer structure further includes a second connecting member 50, which replaces the liquid return channel in the traditional atomizer structure; that is, under normal use state, the liquid 32 at the bottom of the first cavity 21 can flow back into the bottle body 30 through the second connecting member 50. However, under abnormal use states, that is, when tilted to the side, inverted, and/or shaken as described above, the second connecting member 50 is configured to prevent liquid 32 contained in the second cavity 31 from flowing into the first cavity 21 when the container structure is tilted to the side, inverted, and/or shaken, when the bottle body 30 is connected to the spray assembly 20. Thereby, it is prevented that the liquid 32 in the bottle body 30 flows out of the atomizer structure in the abnormal use states, which causes the waste of the liquid 32 (for example, essential oil).

Optionally, the second connecting member 50 is preferably a one-way valve 50c. The one-way valve 50c can only flow in one direction, that is, when the air pressure of the first cavity 21 is greater than that of the second cavity 31, the one-way 50c communicates the first cavity 21 and the second cavity 31; and when the air pressure of the first cavity 21 is less than or equal to the pressure of the second cavity 31, the one-way valve 50c blocks the communication between the first cavity 21 and the second cavity 31.

Embodiment 4

Figure 9:
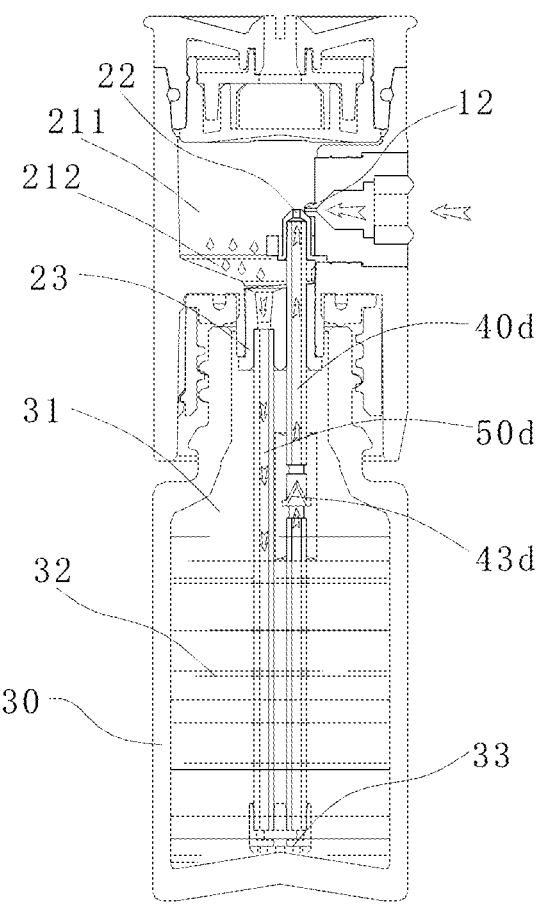
FIG. 9 is a cross-sectional view of an atomizer structure provided by a fourth embodiment of the present application, the atomizer structure is in use state.
Figure 10:
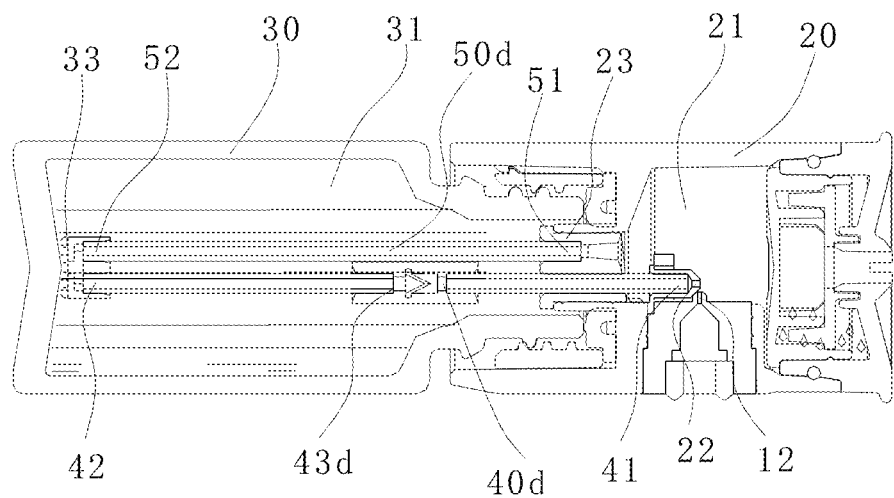
FIG. 10 is a cross-sectional view of an atomizer structure provided by a fourth embodiment of the present application, the atomizer structure is not in a non-use state of horizontally tilted.

FIGS. 9 and 10 show the fourth embodiment of the atomizer structure and the atomizer having the same provided by the present application. FIGS. 9 and 10 refer to the similar structural state descriptions in the first embodiment.

In the embodiment, the atomizer structure includes a gas supplying assembly, which includes an air pump 10, an air tube 11 connected to the air pump 10, and a gas nozzle 12 connected to the end of the air tube 11. The atomizer structure also includes a spray assembly 20 and a bottle body 30 connected to the spray assembly 20. The bottle body 30 is configured to contain the liquid 32 and is configured to be connectable to the spray assembly 20, and the bottle body 30 includes a second cavity 31; the spray assembly 20 includes a first cavity 21 for atomizing the liquid 32, a plurality of mist outlet holes 25 communicating with the first cavity 21, and a liquid nozzle 22 arranged in the first cavity 21. In the embodiment, the outlet end of the gas nozzle 12 is located in the first cavity 21 such that the gas outlet of the gas nozzle 12 faces the liquid outlet of the liquid nozzle 22; that is, the gas blown from the gas pump 10 through the air tube 11 blows directly to the liquid nozzle 22 and enters the first cavity 21.

In the embodiment, the gas outlet of the gas nozzle 12 is located adjacent to the liquid outlet of the liquid nozzle 22, and is configured to guide the airflow leaving the gas pump 10 to the liquid outlet of the liquid nozzle 22, therefore, when the air pump 10 provides a high-pressure airflow and ejects the airflow from the gas nozzle 12, a negative pressure is formed at the upper end of the liquid nozzle 22 to extract liquid 32 (eg, essential oil) from the bottle body 30 through the liquid nozzle 22. Then, the extracted essential oil droplets can be atomized by the high-speed airflow from the gas nozzle 12 to form a mixed airflow containing essential oil droplets; finally, a suitable atomized airflow is diffused into the surrounding atmosphere.

In a preferred embodiment of the present application, the outlet of the gas outlet of the gas nozzle 12 axially points to the top of the upper end of the side wall of the liquid nozzle 22. Further preferably, the outlet axis of the gas nozzle 12 and the outlet axis of the liquid nozzle 22 form an angle of less than 90 degrees. Furthermore, when the airflow is ejected from the gas outlet of the gas nozzle 12, the airflow can cover the upper end of the liquid nozzle 22 to form a better negative pressure at the upper end of the liquid nozzle 22 (for example, due to the Bernoulli effect), which can facilitate extracting liquid 32, such as essential oil, from the bottle body 30. Therefore, the top of the side wall of the liquid nozzle 22 can change the direction of the airflow ejected from the gas nozzle 12 (for example, by blocking at least some of the airflow), thereby improving the atomization of the essential oil droplets sucked from the liquid nozzle 22.

In the embodiment, the atomizer structure further includes a first connecting member 40 that communicates with the first cavity 21 and the second cavity 31 and is configured to allow the liquid 32 contained in the second cavity 31 entering the first cavity 21, when the air pressure of the first cavity 21 is lower than the air pressure of the second cavity 31. The first connecting member 40 communicates the first cavity 21 and the second cavity 31 in a natural state, that is, in a normal use state, and the liquid 32 in the bottle body 30 can enter the first cavity 21 through the first connecting member 40 and then being atomized.

Optionally, the first connecting member 40 is preferably a liquid suction tube 40d connected between the first cavity 21 and the second cavity 31. The liquid suction tube 40d includes a first end 41 located at the upper part and a second end 42 opposite to the first end 41, and the first end 41 extends into the first cavity 21, such that in a normal state, the horizontal height of the first end 41 is higher that the horizontal height of the bottom surface of the first cavity 21; that is, the first end 41 extends into the inside of the first cavity 21. The second end 42 can extend into the second cavity 31. Here, the second end 42 is preferably approximately close to the bottom surface inside the bottle body 30, and ensures that there is a gap between the second end 42 and the bottom surface inside of the bottle body 30 for the liquid 32 to circulate.

In the embodiment, the liquid suction pipe 40d is further provided with a duckbill valve 43d, and the duckbill valve 43d is configured to allow the liquid 32 to enter the first cavity 21 from the second cavity 31 and communicate with each other, while blocks the communication of the first cavity 21 to the second cavity 31. When the atomizer structure is not in use, since there is no interference from the air pump 10, the air pressure between the first cavity 21 and the second cavity 31 is balanced, and the liquid 32 in the second cavity 31 will not be sucked and entered the first cavity 21 through the liquid suction tube 40d and/or the second connecting member 50; and due to the existence of the duckbill valve 43d, the liquid 32 is prevented from flowing into the second cavity 31 from the first cavity 21 via the liquid suction pipe 40d. Furthermore, the air pressure balance between the first cavity 21 and the second cavity 31 will not be affected.

In the embodiment, the atomizer structure further includes a second connecting member 50, which replaces the liquid return channel in the traditional atomizer structure; that is, under normal use state, the liquid 32 at the bottom of the first cavity 21 can flow back into the bottle body 30 through the second connecting member 50. However, under abnormal use states, that is, when tilted to the side, inverted, and/or shaken as described above, the second connecting member 50 is configured to prevent liquid 32 contained in the second cavity 31 from flowing into the first cavity 21 when the container structure is tilted to the side, inverted, and/or shaken, when the bottle body 30 is connected to the spray assembly 20. Thereby, it is prevented that the liquid 32 in the bottle body 30 flows out of the atomizer structure in the abnormal use states, which causes the waste of the liquid 32 (for example, essential oil).

Optionally, the second connecting member 50 is preferably a liquid return tube 50d connected between the first cavity 21 and the second cavity 31. In the embodiment, the number of the liquid return tube 50d is at least one. The liquid return tube 50d includes a third end 51 located at the upper part and a fourth end 52 opposite to the third end 51. In the embodiment, in the normal structure of the atomizer, the horizontal height of the third end 51 is smaller than that of the first end 41.

In an alternative embodiment, the opening of the third end 51 is located at the bottom of the first cavity 21; here, the opening of the third end 51 may be aligned with the bottom of the first cavity 21, or the horizontal height of the opening of the third end 51 is lower than the horizontal height of the bottom of the first cavity 21.

In the embodiment, the fourth end 52 can extend into the second cavity 31. Here, the length of the liquid return tube 50d extending into the second cavity 31 is preferably equal to that of the liquid suction tube 40a; that is, the fourth end 52 is preferably approximately close to the bottom surface of the bottle body 30, and it is ensured that there is a gap between the fourth end 52 and the bottom surface inside of the bottle body 30 for the liquid 32 to circulate.

Embodiment 5

Figure 11:
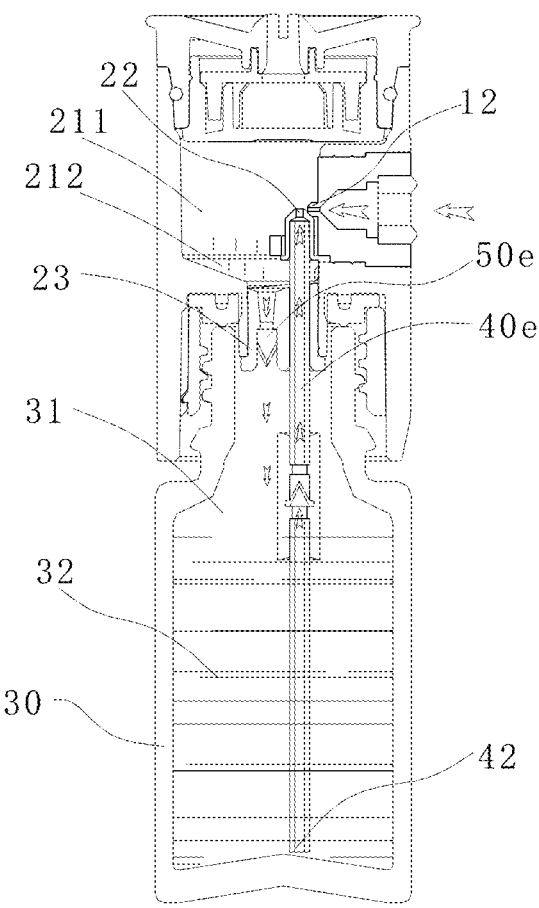
FIG. 11 is a cross-sectional view of an atomizer structure provided by a fifth embodiment of the present application, the atomizer structure is in use state.
Figure 12:
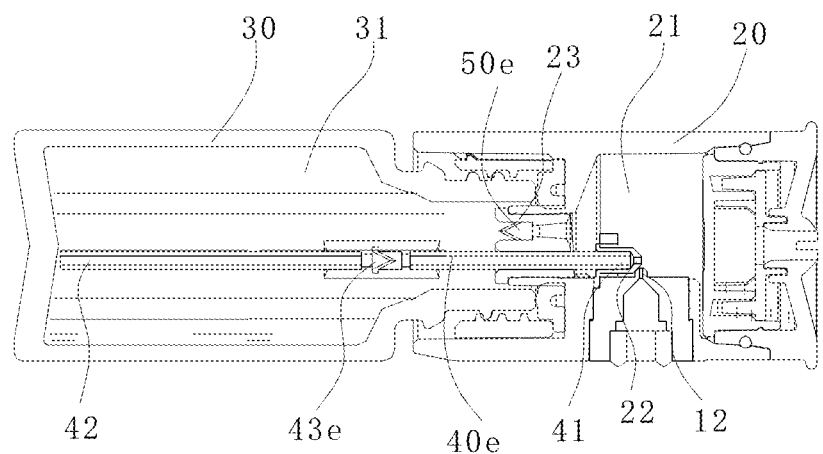
FIG. 12 is a cross-sectional view of an atomizer structure provided by a fifth embodiment of the present application, the atomizer structure is not in a non-use state of horizontally tilted.

FIGS. 11 and 12 show the fifth embodiment of the atomizer structure and the atomizer having the same provided by the present application. FIGS. 11 and 12 refer to the similar structural state descriptions in the first embodiment.

In the embodiment, the atomizer structure includes a gas supplying assembly, which includes an air pump 10, an air tube 11 connected to the air pump 10, and a gas nozzle 12 connected to the end of the air tube 11. The atomizer structure also includes a spray assembly 20 and a bottle body 30 connected to the spray assembly 20. The bottle body 30 is configured to contain the liquid 32 and is configured to be connectable to the spray assembly 20, and the bottle body 30 includes a second cavity 31; the spray assembly 20 includes a first cavity 21 for atomizing the liquid 32, a plurality of mist outlet holes 25 communicating with the first cavity 21, and a liquid nozzle 22 arranged in the first cavity 21. In the embodiment, the outlet end of the gas nozzle 12 is located in the first cavity 21 such that the gas outlet of the gas nozzle 12 faces the liquid outlet of the liquid nozzle 22; that is, the gas blown from the gas pump 10 through the air tube 11 blows directly to the liquid nozzle 22 and enters the first cavity 21.

In the embodiment, the gas outlet of the gas nozzle 12 is located adjacent to the liquid outlet of the liquid nozzle 22, and is configured to guide the airflow leaving the gas pump 10 to the liquid outlet of the liquid nozzle 22, therefore, when the air pump 10 provides a high-pressure airflow and ejects the airflow from the gas nozzle 12, a negative pressure is formed at the upper end of the liquid nozzle 22 to extract liquid 32 (eg, essential oil) from the bottle body 30 through the liquid nozzle 22. Then, the extracted essential oil droplets can be atomized by the high-speed airflow from the gas nozzle 12 to form a mixed airflow containing essential oil droplets; finally, a suitable atomized airflow is diffused into the surrounding atmosphere.

In a preferred embodiment of the present application, the outlet of the gas outlet of the gas nozzle 12 axially points to the top of the upper end of the side wall of the liquid nozzle 22. Further preferably, the outlet axis of the gas nozzle 12 and the outlet axis of the liquid nozzle 22 form an angle of less than 90 degrees. Furthermore, when the airflow is ejected from the gas outlet of the gas nozzle 12, the airflow can cover the upper end of the liquid nozzle 22 to form a better negative pressure at the upper end of the liquid nozzle 22 (for example, due to the Bernoulli effect), which can facilitate extracting liquid 32, such as essential oil, from the bottle body 30. Therefore, the top of the side wall of the liquid nozzle 22 can change the direction of the airflow ejected from the gas nozzle 12 (for example, by blocking at least some of the airflow), thereby improving the atomization of the essential oil droplets sucked from the liquid nozzle 22.

In the embodiment, the atomizer structure further includes a first connecting member 40 that communicates with the first cavity 21 and the second cavity 31 and is configured to allow the liquid 32 contained in the second cavity 31 entering the first cavity 21, when the air pressure of the first cavity 21 is lower than the air pressure of the second cavity 31. The first connecting member 40 communicates the first cavity 21 and the second cavity 31 in a natural state, that is, in a normal use state, and the liquid 32 in the bottle body 30 can enter the first cavity 21 through the first connecting member 40 and then being atomized.

Optionally, the first connecting member 40 is preferably a liquid suction tube 40e connected between the first cavity 21 and the second cavity 31. The liquid suction tube 40e includes a first end 41 located at the upper part and a second end 42 opposite to the first end 41, and the first end 41 extends into the first cavity 21, such that in a normal state, the horizontal height of the first end 41 is higher that the horizontal height of the bottom surface of the first cavity 21; that is, the first end 41 extends into the inside of the first cavity 21. The second end 42 can extend into the second cavity 31. Here, the second end 42 is preferably approximately close to the bottom surface inside the bottle body 30, and ensures that there is a gap between the second end 42 and the bottom surface inside of the bottle body 30 for the liquid 32 to circulate.

In the embodiment, the liquid suction pipe 40e is further provided with a duckbill valve 43e, and the duckbill valve 43e is configured to allow the liquid 32 to enter the first cavity 21 from the second cavity 31 and communicate with each other, while blocks the communication of the first cavity 21 to the second cavity 31. When the atomizer structure is not in use, since there is no interference from the air pump 10, the air pressure between the first cavity 21 and the second cavity 31 is balanced, and the liquid 32 in the second cavity 31 will not be sucked and entered the first cavity 21 through the liquid suction tube 40e and/or the second connecting member 50; and due to the existence of the duckbill valve 43e, the liquid 32 is prevented from flowing into the second cavity 31 from the first cavity 21 via the liquid suction pipe 40e. Furthermore, the air pressure balance between the first cavity 21 and the second cavity 31 will not be affected.

In the embodiment, the atomizer structure further includes a second connecting member 50, which replaces the liquid return channel in the traditional atomizer structure; that is, under normal use state, the liquid 32 at the bottom of the first cavity 21 can flow back into the bottle body 30 through the second connecting member 50. However, under abnormal use states, that is, when tilted to the side, inverted, and/or shaken as described above, the second connecting member 50 is configured to prevent liquid 32 contained in the second cavity 31 from flowing into the first cavity 21 when the container structure is tilted to the side, inverted, and/or shaken, when the bottle body 30 is connected to the spray assembly 20. Thereby, it is prevented that the liquid 32 in the bottle body 30 flows out of the atomizer structure in the abnormal use states, which causes the waste of the liquid 32 (for example, essential oil).

Optionally, the second connecting member 50 is preferably a duckbill valve 50e. The duckbill valve 50e can only flow in one direction, that is, when the air pressure of the first cavity 21 is greater than that of the second cavity 31, the duckbill valve 50e communicates the first cavity 21 and the second cavity 31; and when the air pressure of the first cavity 21 is less than or equal to the pressure of the second cavity 31, the duckbill valve 50e blocks the communication between the first cavity 21 and the second cavity 31.

Embodiment 6

Figure 13:
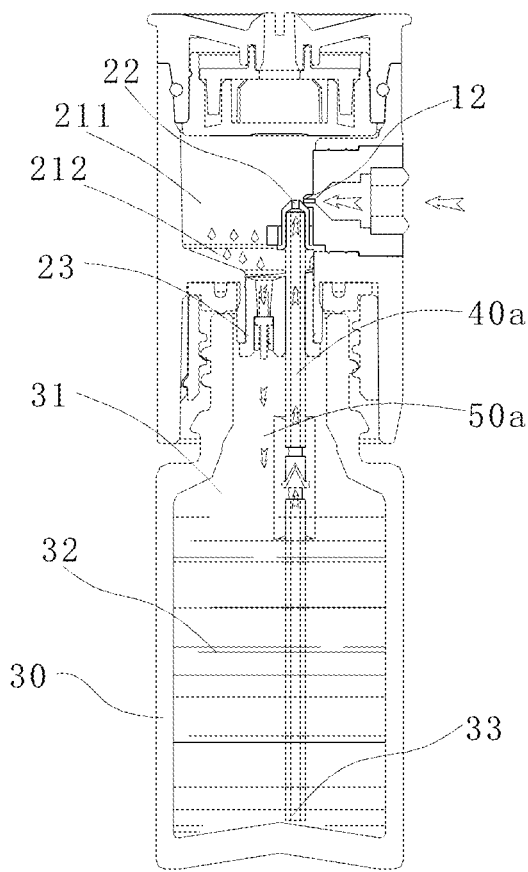
FIG. 13 is a cross-sectional view of an atomizer structure provided by a sixth embodiment of the present application, the atomizer structure is in use state.
Figure 14:
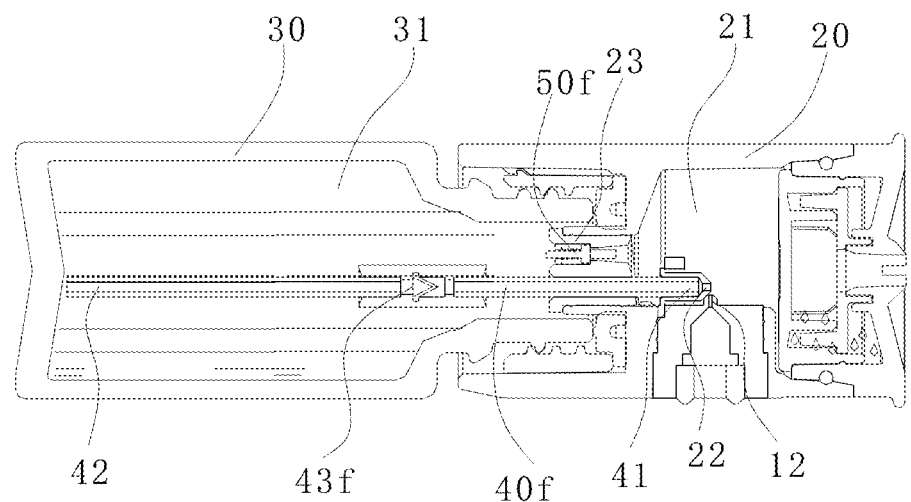
FIG. 14 is a cross-sectional view of an atomizer structure provided by a sixth embodiment of the present application, the atomizer structure is not in a non-use state of horizontally tilted.

FIGS. 13 and 14 show the sixth embodiment of the atomizer structure and the atomizer having the same provided by the present application. FIGS. 13 and 14 refer to the similar structural state descriptions in the first embodiment.

In the embodiment, the atomizer structure includes a gas supplying assembly, which includes an air pump 10, an air tube 11 connected to the air pump 10, and a gas nozzle 12 connected to the end of the air tube 11. The atomizer structure also includes a spray assembly 20 and a bottle body 30 connected to the spray assembly 20. The bottle body 30 is configured to contain the liquid 32 and is configured to be connectable to the spray assembly 20, and the bottle body 30 includes a second cavity 31; the spray assembly 20 includes a first cavity 21 for atomizing the liquid 32, a plurality of mist outlet holes 25 communicating with the first cavity 21, and a liquid nozzle 22 arranged in the first cavity 21. In the embodiment, the outlet end of the gas nozzle 12 is located in the first cavity 21 such that the gas outlet of the gas nozzle 12 faces the liquid outlet of the liquid nozzle 22; that is, the gas blown from the gas pump 10 through the air tube 11 blows directly to the liquid nozzle 22 and enters the first cavity 21.

In the embodiment, the gas outlet of the gas nozzle 12 is located adjacent to the liquid outlet of the liquid nozzle 22, and is configured to guide the airflow leaving the gas pump 10 to the liquid outlet of the liquid nozzle 22, therefore, when the air pump 10 provides a high-pressure airflow and ejects the airflow from the gas nozzle 12, a negative pressure is formed at the upper end of the liquid nozzle 22 to extract liquid 32 (eg, essential oil) from the bottle body 30 through the liquid nozzle 22. Then, the extracted essential oil droplets can be atomized by the high-speed airflow from the gas nozzle 12 to form a mixed airflow containing essential oil droplets; finally, a suitable atomized airflow is diffused into the surrounding atmosphere.

In a preferred embodiment of the present application, the outlet of the gas outlet of the gas nozzle 12 axially points to the top of the upper end of the side wall of the liquid nozzle 22. Further preferably, the outlet axis of the gas nozzle 12 and the outlet axis of the liquid nozzle 22 form an angle of less than 90 degrees. Furthermore, when the airflow is ejected from the gas outlet of the gas nozzle 12, the airflow can cover the upper end of the liquid nozzle 22 to form a better negative pressure at the upper end of the liquid nozzle 22 (for example, due to the Bernoulli effect), which can facilitate extracting liquid 32, such as essential oil, from the bottle body 30. Therefore, the top of the side wall of the liquid nozzle 22 can change the direction of the airflow ejected from the gas nozzle 12 (for example, by blocking at least some of the airflow), thereby improving the atomization of the essential oil droplets sucked from the liquid nozzle 22.

In the embodiment, the atomizer structure further includes a first connecting member 40 that communicates with the first cavity 21 and the second cavity 31 and is configured to allow the liquid 32 contained in the second cavity 31 entering the first cavity 21, when the air pressure of the first cavity 21 is lower than the air pressure of the second cavity 31. The first connecting member 40 communicates the first cavity 21 and the second cavity 31 in a natural state, that is, in a normal use state, and the liquid 32 in the bottle body 30 can enter the first cavity 21 through the first connecting member 40 and then being atomized.

Optionally, the first connecting member 40 is preferably a liquid suction tube 40f connected between the first cavity 21 and the second cavity 31. The liquid suction tube 40f includes a first end 41 located at the upper part and a second end 42 opposite to the first end 41, and the first end 41 extends into the first cavity 21, such that in a normal state, the horizontal height of the first end 41 is higher that the horizontal height of the bottom surface of the first cavity 21; that is, the first end 41 extends into the inside of the first cavity 21. The second end 42 can extend into the second cavity 31. Here, the second end 42 is preferably approximately close to the bottom surface inside the bottle body 30, and ensures that there is a gap between the second end 42 and the bottom surface inside of the bottle body 30 for the liquid 32 to circulate.

In the embodiment, the liquid suction pipe 40f is further provided with a duckbill valve 43f, and the duckbill valve 43f is configured to allow the liquid 32 to enter the first cavity 21 from the second cavity 31 and communicate with each other, while blocks the communication of the first cavity 21 to the second cavity 31. When the atomizer structure is not in use, since there is no interference from the air pump 10, the air pressure between the first cavity 21 and the second cavity 31 is balanced, and the liquid 32 in the second cavity 31 will not be sucked and entered the first cavity 21 through the liquid suction tube 40f and/or the second connecting member 50; and due to the existence of the duckbill valve 43f, the liquid 32 is prevented from flowing into the second cavity 31 from the first cavity 21 via the liquid suction pipe 40f. Furthermore, the air pressure balance between the first cavity 21 and the second cavity 31 will not be affected.

In the embodiment, the atomizer structure further includes a second connecting member 50, which replaces the liquid return channel in the traditional atomizer structure; that is, under normal use state, the liquid 32 at the bottom of the first cavity 21 can flow back into the bottle body 30 through the second connecting member 50. However, under abnormal use states, that is, when tilted to the side, inverted, and/or shaken as described above, the second connecting member 50 is configured to prevent liquid 32 contained in the second cavity 31 from flowing into the first cavity 21 when the container structure is tilted to the side, inverted, and/or shaken, when the bottle body 30 is connected to the spray assembly 20. Thereby, it is prevented that the liquid 32 in the bottle body 30 flows out of the atomizer structure in the abnormal use states, which causes the waste of the liquid 32 (for example, essential oil).

Optionally, the second connecting member 50 is preferably a one-way valve 50f. The one-way valve 50f can only flow in one direction, that is, when the air pressure of the first cavity 21 is greater than that of the second cavity 31, the one-way 50f communicates the first cavity 21 and the second cavity 31; and when the air pressure of the first cavity 21 is less than or equal to the pressure of the second cavity 31, the one-way valve 50f blocks the communication between the first cavity 21 and the second cavity 31.

Embodiment 7

Figure 15:
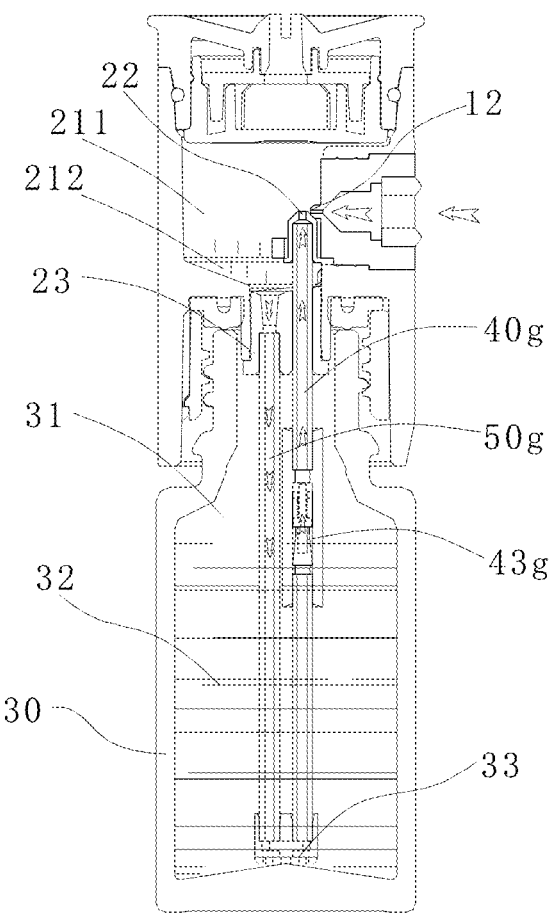
FIG. 15 is a cross-sectional view of an atomizer structure provided by a seventh embodiment of the present application, the atomizer structure is in use state.
Figure 16:
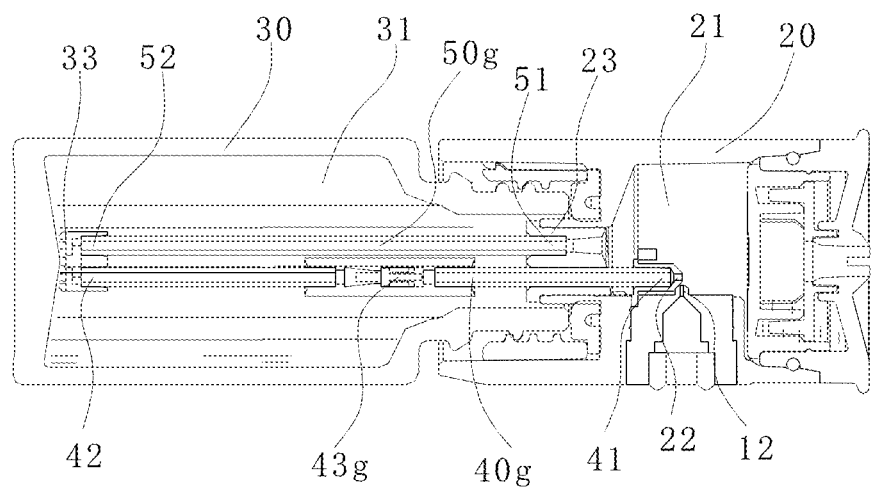
FIG. 16 is a cross-sectional view of an atomizer structure provided by a seventh embodiment of the present application, the atomizer structure is not in a non-use state of horizontally tilted.

FIGS. 15 and 16 show the seventh embodiment of the atomizer structure and the atomizer having the same provided by the present application. FIGS. 15 and 16 refer to the similar structural state descriptions in the first embodiment.

In the embodiment, the atomizer structure includes a gas supplying assembly, which includes an air pump 10, an air tube 11 connected to the air pump 10, and a gas nozzle 12 connected to the end of the air tube 11. The atomizer structure also includes a spray assembly 20 and a bottle body 30 connected to the spray assembly 20. The bottle body 30 is configured to contain the liquid 32 and is configured to be connectable to the spray assembly 20, and the bottle body 30 includes a second cavity 31; the spray assembly 20 includes a first cavity 21 for atomizing the liquid 32, a plurality of mist outlet holes 25 communicating with the first cavity 21, and a liquid nozzle 22 arranged in the first cavity 21. In the embodiment, the outlet end of the gas nozzle 12 is located in the first cavity 21 such that the gas outlet of the gas nozzle 12 faces the liquid outlet of the liquid nozzle 22; that is, the gas blown from the gas pump 10 through the air tube 11 blows directly to the liquid nozzle 22 and enters the first cavity 21.

In the embodiment, the gas outlet of the gas nozzle 12 is located adjacent to the liquid outlet of the liquid nozzle 22, and is configured to guide the airflow leaving the gas pump 10 to the liquid outlet of the liquid nozzle 22, therefore, when the air pump 10 provides a high-pressure airflow and ejects the airflow from the gas nozzle 12, a negative pressure is formed at the upper end of the liquid nozzle 22 to extract liquid 32 (eg, essential oil) from the bottle body 30 through the liquid nozzle 22. Then, the extracted essential oil droplets can be atomized by the high-speed airflow from the gas nozzle 12 to form a mixed airflow containing essential oil droplets; finally, a suitable atomized airflow is diffused into the surrounding atmosphere.

In a preferred embodiment of the present application, the outlet of the gas outlet of the gas nozzle 12 axially points to the top of the upper end of the side wall of the liquid nozzle 22. Further preferably, the outlet axis of the gas nozzle 12 and the outlet axis of the liquid nozzle 22 form an angle of less than 90 degrees. Furthermore, when the airflow is ejected from the gas outlet of the gas nozzle 12, the airflow can cover the upper end of the liquid nozzle 22 to form a better negative pressure at the upper end of the liquid nozzle 22 (for example, due to the Bernoulli effect), which can facilitate extracting liquid 32, such as essential oil, from the bottle body 30. Therefore, the top of the side wall of the liquid nozzle 22 can change the direction of the airflow ejected from the gas nozzle 12 (for example, by blocking at least some of the airflow), thereby improving the atomization of the essential oil droplets sucked from the liquid nozzle 22.

In the embodiment, the atomizer structure further includes a first connecting member 40 that communicates with the first cavity 21 and the second cavity 31 and is configured to allow the liquid 32 contained in the second cavity 31 entering the first cavity 21, when the air pressure of the first cavity 21 is lower than the air pressure of the second cavity 31. The first connecting member 40 communicates the first cavity 21 and the second cavity 31 in a natural state, that is, in a normal use state, and the liquid 32 in the bottle body 30 can enter the first cavity 21 through the first connecting member 40 and then being atomized.

Optionally, the first connecting member 40 is preferably a liquid suction tube 40g connected between the first cavity 21 and the second cavity 31. The liquid suction tube 40g includes a first end 41 located at the upper part and a second end 42 opposite to the first end 41, and the first end 41 extends into the first cavity 21, such that in a normal state, the horizontal height of the first end 41 is higher that the horizontal height of the bottom surface of the first cavity 21; that is, the first end 41 extends into the inside of the first cavity 21. The second end 42 can extend into the second cavity 31. Here, the second end 42 is preferably approximately close to the bottom surface inside the bottle body 30, and ensures that there is a gap between the second end 42 and the bottom surface inside of the bottle body 30 for the liquid 32 to circulate.

In the embodiment, the liquid suction pipe 40g is further provided with a one-way valve 43g, and the one-way valve 43g is configured to allow the liquid 32 to enter the first cavity 21 from the second cavity 31 and communicate with each other, while blocks the communication of the first cavity 21 to the second cavity 31. When the atomizer structure is not in use, since there is no interference from the air pump 10, the air pressure between the first cavity 21 and the second cavity 31 is balanced, and the liquid 32 in the second cavity 31 will not be sucked and entered the first cavity 21 through the liquid suction tube 40g and/or the second connecting member 50; and due to the existence of the duckbill valve 43g, the liquid 32 is prevented from flowing into the second cavity 31 from the first cavity 21 via the liquid suction pipe 40g. Furthermore, the air pressure balance between the first cavity 21 and the second cavity 31 will not be affected.

In the embodiment, the atomizer structure further includes a second connecting member 50, which replaces the liquid return channel in the traditional atomizer structure; that is, under normal use state, the liquid 32 at the bottom of the first cavity 21 can flow back into the bottle body 30 through the second connecting member 50. However, under abnormal use states, that is, when tilted to the side, inverted, and/or shaken as described above, the second connecting member 50 is configured to prevent liquid 32 contained in the second cavity 31 from flowing into the first cavity 21 when the container structure is tilted to the side, inverted, and/or shaken, when the bottle body 30 is connected to the spray assembly 20. Thereby, it is prevented that the liquid 32 in the bottle body 30 flows out of the atomizer structure in the abnormal use states, which causes the waste of the liquid 32 (for example, essential oil).

Optionally, the second connecting member 50 is preferably a liquid return tube 50g connected between the first cavity 21 and the second cavity 31. In the embodiment, the number of the liquid return tube 50g is at least one. The liquid return tube 50d includes a third end 51 located at the upper part and a fourth end 52 opposite to the third end 51. In the embodiment, in the normal structure of the atomizer, the horizontal height of the third end 51 is smaller than that of the first end 41.

In an alternative embodiment, the opening of the third end 51 is located at the bottom of the first cavity 21; here, the opening of the third end 51 may be aligned with the bottom of the first cavity 21, or the horizontal height of the opening of the third end 51 is lower than the horizontal height of the bottom of the first cavity 21.

In the embodiment, the fourth end 52 can extend into the second cavity 31. Here, the length of the liquid return tube 50g extending into the second cavity 31 is preferably equal to that of the liquid suction tube 40g; that is, the fourth end 52 is preferably approximately close to the bottom surface of the bottle body 30, and it is ensured that there is a gap between the fourth end 52 and the bottom surface inside of the bottle body 30 for the liquid 32 to circulate.

Embodiment 8

Figure 17:
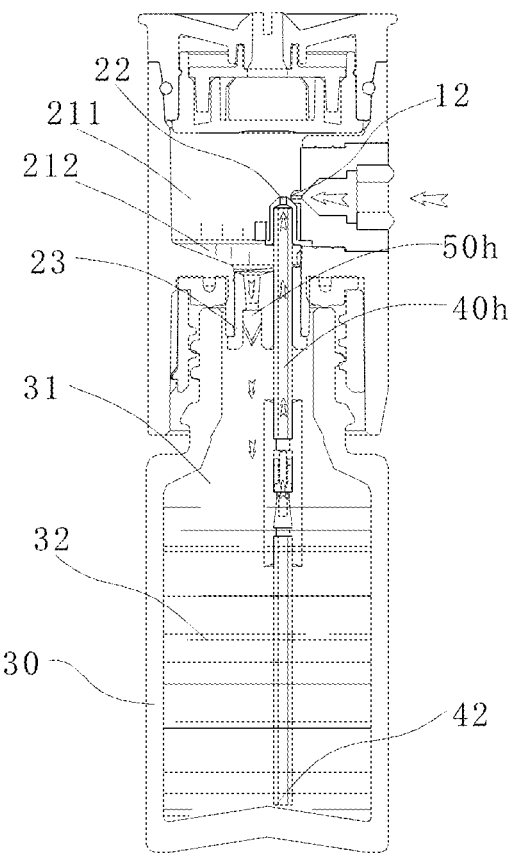
FIG. 17 is a cross-sectional view of an atomizer structure provided by an eighth embodiment of the present application, the atomizer structure is in use state.
Figure 18:
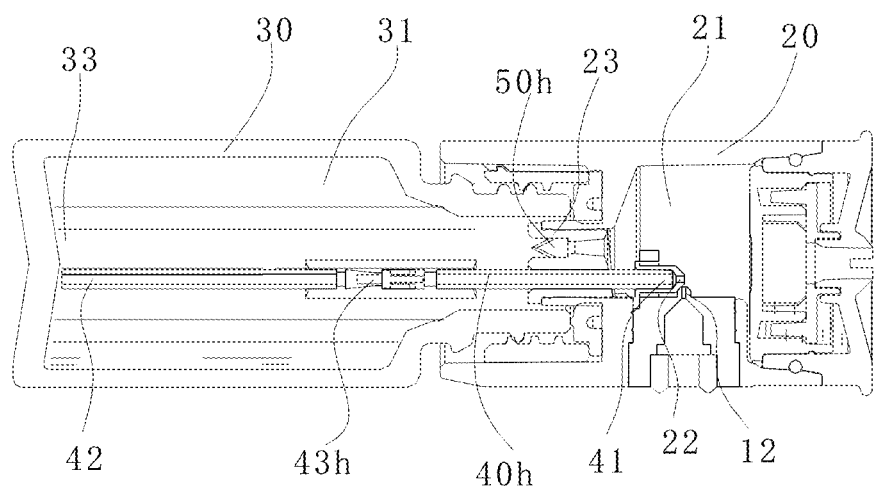
FIG. 18 is a cross-sectional view of an atomizer structure provided by an eighth embodiment of the present application, the atomizer structure is not in a non-use state of horizontally tilted.

FIGS. 17 and 18 show the eighth embodiment of the atomizer structure and the atomizer having the same provided by the present application. FIGS. 17 and 18 refer to the similar structural state descriptions in the first embodiment.

In the embodiment, the atomizer structure includes a gas supplying assembly, which includes an air pump 10, an air tube 11 connected to the air pump 10, and a gas nozzle 12 connected to the end of the air tube 11. The atomizer structure also includes a spray assembly 20 and a bottle body 30 connected to the spray assembly 20. The bottle body 30 is configured to contain the liquid 32 and is configured to be connectable to the spray assembly 20, and the bottle body 30 includes a second cavity 31; the spray assembly 20 includes a first cavity 21 for atomizing the liquid 32, a plurality of mist outlet holes 25 communicating with the first cavity 21, and a liquid nozzle 22 arranged in the first cavity 21. In the embodiment, the outlet end of the gas nozzle 12 is located in the first cavity 21 such that the gas outlet of the gas nozzle 12 faces the liquid outlet of the liquid nozzle 22; that is, the gas blown from the gas pump 10 through the air tube 11 blows directly to the liquid nozzle 22 and enters the first cavity 21.

In the embodiment, the gas outlet of the gas nozzle 12 is located adjacent to the liquid outlet of the liquid nozzle 22, and is configured to guide the airflow leaving the gas pump 10 to the liquid outlet of the liquid nozzle 22, therefore, when the air pump 10 provides a high-pressure airflow and ejects the airflow from the gas nozzle 12, a negative pressure is formed at the upper end of the liquid nozzle 22 to extract liquid 32 (eg, essential oil) from the bottle body 30 through the liquid nozzle 22. Then, the extracted essential oil droplets can be atomized by the high-speed airflow from the gas nozzle 12 to form a mixed airflow containing essential oil droplets; finally, a suitable atomized airflow is diffused into the surrounding atmosphere.

In a preferred embodiment of the present application, the outlet of the gas outlet of the gas nozzle 12 axially points to the top of the upper end of the side wall of the liquid nozzle 22. Further preferably, the outlet axis of the gas nozzle 12 and the outlet axis of the liquid nozzle 22 form an angle of less than 90 degrees. Furthermore, when the airflow is ejected from the gas outlet of the gas nozzle 12, the airflow can cover the upper end of the liquid nozzle 22 to form a better negative pressure at the upper end of the liquid nozzle 22 (for example, due to the Bernoulli effect), which can facilitate extracting liquid 32, such as essential oil, from the bottle body 30. Therefore, the top of the side wall of the liquid nozzle 22 can change the direction of the airflow ejected from the gas nozzle 12 (for example, by blocking at least some of the airflow), thereby improving the atomization of the essential oil droplets sucked from the liquid nozzle 22.

In the embodiment, the atomizer structure further includes a first connecting member 40 that communicates with the first cavity 21 and the second cavity 31 and is configured to allow the liquid 32 contained in the second cavity 31 entering the first cavity 21, when the air pressure of the first cavity 21 is lower than the air pressure of the second cavity 31. The first connecting member 40 communicates the first cavity 21 and the second cavity 31 in a natural state, that is, in a normal use state, and the liquid 32 in the bottle body 30 can enter the first cavity 21 through the first connecting member 40 and then being atomized.

Optionally, the first connecting member 40 is preferably a liquid suction tube 40h connected between the first cavity 21 and the second cavity 31. The liquid suction tube 40h includes a first end 41 located at the upper part and a second end 42 opposite to the first end 41, and the first end 41 extends into the first cavity 21, such that in a normal state, the horizontal height of the first end 41 is higher that the horizontal height of the bottom surface of the first cavity 21; that is, the first end 41 extends into the inside of the first cavity 21. The second end 42 can extend into the second cavity 31. Here, the second end 42 is preferably approximately close to the bottom surface inside the bottle body 30, and ensures that there is a gap between the second end 42 and the bottom surface inside of the bottle body 30 for the liquid 32 to circulate.

In the embodiment, the liquid suction pipe 40h is further provided with a one-way valve 43h, and the one-way valve 43h is configured to allow the liquid 32 to enter the first cavity 21 from the second cavity 31 and communicate with each other, while blocks the communication of the first cavity 21 to the second cavity 31. When the atomizer structure is not in use, since there is no interference from the air pump 10, the air pressure between the first cavity 21 and the second cavity 31 is balanced, and the liquid 32 in the second cavity 31 will not be sucked and entered the first cavity 21 through the liquid suction tube 40h and/or the second connecting member 50; and due to the existence of the duckbill valve 43h, the liquid 32 is prevented from flowing into the second cavity 31 from the first cavity 21 via the liquid suction pipe 40h. Furthermore, the air pressure balance between the first cavity 21 and the second cavity 31 will not be affected.

In the embodiment, the atomizer structure further includes a second connecting member 50, which replaces the liquid return channel in the traditional atomizer structure; that is, under normal use state, the liquid 32 at the bottom of the first cavity 21 can flow back into the bottle body 30 through the second connecting member 50. However, under abnormal use states, that is, when tilted to the side, inverted, and/or shaken as described above, the second connecting member 50 is configured to prevent liquid 32 contained in the second cavity 31 from flowing into the first cavity 21 when the container structure is tilted to the side, inverted, and/or shaken, when the bottle body 30 is connected to the spray assembly 20. Thereby, it is prevented that the liquid 32 in the bottle body 30 flows out of the atomizer structure in the abnormal use states, which causes the waste of the liquid 32 (for example, essential oil).

Optionally, the second connecting member 50 is preferably a duckbill valve 50h. The duckbill valve 50h can only flow in one direction, that is, when the air pressure of the first cavity 21 is greater than that of the second cavity 31, the duckbill valve 50h communicates the first cavity 21 and the second cavity 31; and when the air pressure of the first cavity 21 is less than or equal to the pressure of the second cavity 31, the duckbill valve 50h blocks the communication between the first cavity 21 and the second cavity 31.

Embodiment 9

Figure 19:
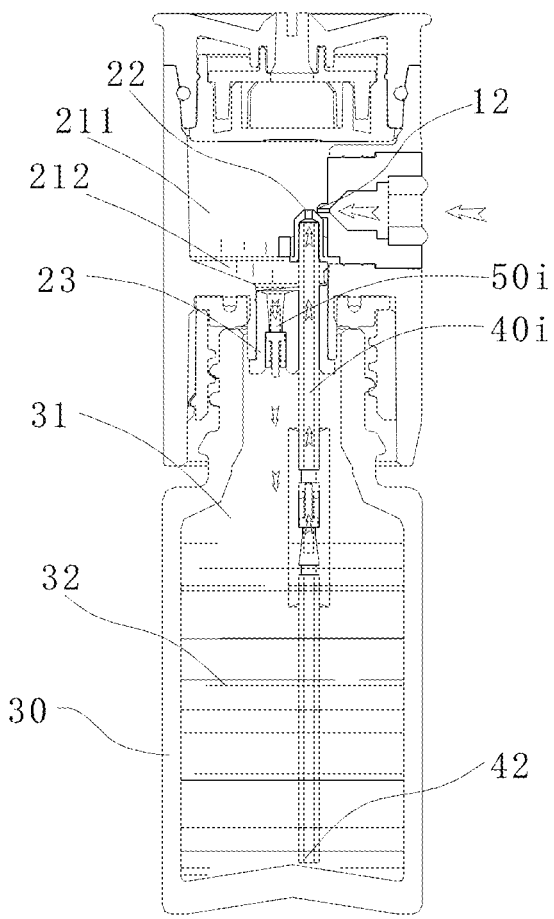
FIG. 19 is a cross-sectional view of an atomizer structure provided by a ninth embodiment of the present application, the atomizer structure is in use state.
Figure 20:
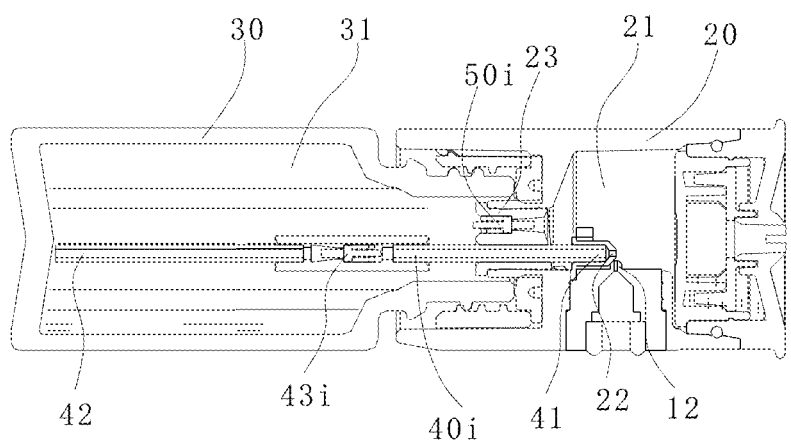
FIG. 20 is a cross-sectional view of an atomizer structure provided by a ninth embodiment of the present application, the atomizer structure is not in a non-use state of horizontally tilted.

FIGS. 19 and 20 show the eighth embodiment of the atomizer structure and the atomizer having the same provided by the present application. FIGS. 19 and 20 refer to the similar structural state descriptions in the first embodiment.

In the embodiment, the atomizer structure includes a gas supplying assembly, which includes an air pump 10, an air tube 11 connected to the air pump 10, and a gas nozzle 12 connected to the end of the air tube 11. The atomizer structure also includes a spray assembly 20 and a bottle body 30 connected to the spray assembly 20. The bottle body 30 is configured to contain the liquid 32 and is configured to be connectable to the spray assembly 20, and the bottle body 30 includes a second cavity 31; the spray assembly 20 includes a first cavity 21 for atomizing the liquid 32, a plurality of mist outlet holes 25 communicating with the first cavity 21, and a liquid nozzle 22 arranged in the first cavity 21. In the embodiment, the outlet end of the gas nozzle 12 is located in the first cavity 21 such that the gas outlet of the gas nozzle 12 faces the liquid outlet of the liquid nozzle 22; that is, the gas blown from the gas pump 10 through the air tube 11 blows directly to the liquid nozzle 22 and enters the first cavity 21.

In the embodiment, the gas outlet of the gas nozzle 12 is located adjacent to the liquid outlet of the liquid nozzle 22, and is configured to guide the airflow leaving the gas pump 10 to the liquid outlet of the liquid nozzle 22, therefore, when the air pump 10 provides a high-pressure airflow and ejects the airflow from the gas nozzle 12, a negative pressure is formed at the upper end of the liquid nozzle 22 to extract liquid 32 (eg, essential oil) from the bottle body 30 through the liquid nozzle 22. Then, the extracted essential oil droplets can be atomized by the high-speed airflow from the gas nozzle 12 to form a mixed airflow containing essential oil droplets; finally, a suitable atomized airflow is diffused into the surrounding atmosphere.

In a preferred embodiment of the present application, the outlet of the gas outlet of the gas nozzle 12 axially points to the top of the upper end of the side wall of the liquid nozzle 22. Further preferably, the outlet axis of the gas nozzle 12 and the outlet axis of the liquid nozzle 22 form an angle of less than 90 degrees. Furthermore, when the airflow is ejected from the gas outlet of the gas nozzle 12, the airflow can cover the upper end of the liquid nozzle 22 to form a better negative pressure at the upper end of the liquid nozzle 22 (for example, due to the Bernoulli effect), which can facilitate extracting liquid 32, such as essential oil, from the bottle body 30. Therefore, the top of the side wall of the liquid nozzle 22 can change the direction of the airflow ejected from the gas nozzle 12 (for example, by blocking at least some of the airflow), thereby improving the atomization of the essential oil droplets sucked from the liquid nozzle 22.

In the embodiment, the atomizer structure further includes a first connecting member 40 that communicates with the first cavity 21 and the second cavity 31 and is configured to allow the liquid 32 contained in the second cavity 31 entering the first cavity 21, when the air pressure of the first cavity 21 is lower than the air pressure of the second cavity 31. The first connecting member 40 communicates the first cavity 21 and the second cavity 31 in a natural state, that is, in a normal use state, and the liquid 32 in the bottle body 30 can enter the first cavity 21 through the first connecting member 40 and then being atomized.

Optionally, the first connecting member 40 is preferably a liquid suction tube 40i connected between the first cavity 21 and the second cavity 31. The liquid suction tube 40i includes a first end 41 located at the upper part and a second end 42 opposite to the first end 41, and the first end 41 extends into the first cavity 21, such that in a normal state, the horizontal height of the first end 41 is higher that the horizontal height of the bottom surface of the first cavity 21; that is, the first end 41 extends into the inside of the first cavity 21. The second end 42 can extend into the second cavity 31. Here, the second end 42 is preferably approximately close to the bottom surface inside the bottle body 30, and ensures that there is a gap between the second end 42 and the bottom surface inside of the bottle body 30 for the liquid 32 to circulate.

In the embodiment, the liquid suction pipe 40i is further provided with a one-way valve 43i, and the one-way valve 43i is configured to allow the liquid 32 to enter the first cavity 21 from the second cavity 31 and communicate with each other, while blocks the communication of the first cavity 21 to the second cavity 31. When the atomizer structure is not in use, since there is no interference from the air pump 10, the air pressure between the first cavity 21 and the second cavity 31 is balanced, and the liquid 32 in the second cavity 31 will not be sucked and entered the first cavity 21 through the liquid suction tube 40i and/or the second connecting member 50; and due to the existence of the duckbill valve 43h, the liquid 32 is prevented from flowing into the second cavity 31 from the first cavity 21 via the liquid suction pipe 40h. Furthermore, the air pressure balance between the first cavity 21 and the second cavity 31 will not be affected.

In the embodiment, the atomizer structure further includes a second connecting member 50, which replaces the liquid return channel in the traditional atomizer structure; that is, under normal use state, the liquid 32 at the bottom of the first cavity 21 can flow back into the bottle body 30 through the second connecting member 50. However, under abnormal use states, that is, when tilted to the side, inverted, and/or shaken as described above, the second connecting member 50 is configured to prevent liquid 32 contained in the second cavity 31 from flowing into the first cavity 21 when the container structure is tilted to the side, inverted, and/or shaken, when the bottle body 30 is connected to the spray assembly 20. Thereby, it is prevented that the liquid 32 in the bottle body 30 flows out of the atomizer structure in the abnormal use states, which causes the waste of the liquid 32 (for example, essential oil).

Optionally, the second connecting member 50 is preferably a one-way valve 50i. The one-way valve 50i can only flow in one direction, that is, when the air pressure of the first cavity 21 is greater than that of the second cavity 31, the one-way 50i communicates the first cavity 21 and the second cavity 31; and when the air pressure of the first cavity 21 is less than or equal to the pressure of the second cavity 31, the one-way valve 50i blocks the communication between the first cavity 21 and the second cavity 31.

In the present application, the atomizer structure is provided with the first connecting member 40 and the second connecting member 50, and in a non-use state, the first cavity 21 and the second cavity 31 are maintained air pressure balance due that the communication of the first connecting member 40 and the second connecting member 50, and the second connecting member 50 is configured to prevent the liquid 32 contained in the second cavity 31 from flowing into the first cavity 21 when the atomizer structure is tilted or inverted, that is, after the atomizer structure is tilted or during the atomizer structure is tilting, since there is no external air pressure interference, the air pressure in the first cavity 21 and the second cavity 31 will not change, thereby the liquid 32 contained in the bottle body 30 will not enter the first cavity 21 through the first connecting member 40, in addition, due to the arrangement of the second connecting member 50, the liquid 32 contained in the bottle body 30 will not enter the first cavity 21 through the second connecting member 50; therefore, when the atomizer structure is not in use, the problem that the liquid 32 contained in the bottle body 30 leaks after being knocked down due to accidental touch and other reasons can be avoided.

The present application further provides an atomizer, as shown in FIG. 1, and the atomizer includes any one of more of the atomizer structure provided by embodiments 1-9. The atomizer further includes a power supply assembly 60 configured to supply power to the atomizer structure, and a controller 61 electrically connected to the power supply assembly 60, the controller 61 including a tilting switch 62 configured to disconnect the power supply assembly 60 from supplying power to the atomizer structure when the atomizer structure is tilted or inverted.

In the present application, with the arrangement of the atomizer structure, when the atomizer structure is not in use, the problem that the liquid 32 contained in the bottle body 30 leaks after being knocked down due to accidental touch and other reasons can be avoided. In addition, with the arrangement of the tilting switch, when the atomizer in use is knocked down, the tilting switch 62 stops the power supply assembly 60 to power the atomizer structure, and the atomizer structure enters the non-use state, therefore, when the atomizer is in use, the problem that the liquid 32 contained in the bottle body 30 leaks after being knocked down due to accidental touch and other reasons can be avoided.

The present description provides examples, and is not limiting of the scope, applicability, or configuration set forth in the claims. Thus, it will be understood that changes may be made in the function and arrangement of elements discussed without departing from the spirit and scope of the disclosure, and various embodiments may omit, substitute, or add other procedures or components as appropriate. For instance, the methods described may be performed in an order different from that described, and various steps may be added, omitted, or combined. Also, features described with respect to certain embodiments may be combined in other embodiments.

Various inventions have been described herein with reference to certain specific embodiments and examples. However, they will be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "comprising."

What is claimed is:
1. An atomizer structure comprising:
a spray assembly comprising a first cavity;
a bottle body, configured to be connectable to the spray assembly, wherein the bottle body comprises a second cavity configured for containing liquid;
a first connecting member communicating the first cavity and the second cavity and configured for guiding a quantity of liquid contained in the second cavity to enter the first cavity when an air pressure in the first cavity is larger than an air pressure in the second cavity, wherein an upper end of the first connecting member is located in the first cavity, and a liquid nozzle is further provided at the upper end;
a gas supplying assembly, the gas supplying assembly comprising an air pump and an air tube connected to an outlet of the air pump, an other end of the air tube is connected with a gas nozzle, and a front end of the gas nozzle extends into the first cavity such that an opening of the gas nozzle faces an opening of the liquid nozzle;
a second connecting member selectively communicating the first cavity and the second cavity such that a quantity of remaining liquid in the first cavity can enter the second cavity when an air pressure in the first cavity is larger than an air pressure in the second cavity, and configured for preventing the liquid in the second cavity from flowing into the first cavity when the atomizer structure is tilted or inverted while gas is not being supplied to the first cavity via the gas nozzle;
wherein the first connecting member is a liquid suction tube connected between the first cavity and the second cavity; and the second connecting member is a liquid return tube, connected between the first cavity and the second cavity; wherein the liquid suction tube and the liquid return tube are configured for keeping the air pressure of the first cavity equal to the air pressure of the second cavity when the gas is not being supplied to the first cavity via the gas nozzle;
wherein the liquid suction tube comprises a first end and a second end, the first end extending into the first cavity, and the second end can extend into the second cavity, the atomizer structure causes the air pressure of the first cavity to be greater than the air pressure of the second cavity when in use, and creates a negative pressure at a port at the first end to allow the liquid contained in the second cavity to flow into the first cavity through the liquid suction tube; and the liquid return tube comprises a third end and a fourth end, an opening of the third end being located at a bottom of the first cavity, and the fourth end can extend into the second cavity; wherein the second end and the fourth end are both connected to a holder;

wherein diameters of the liquid suction tube and the liquid return tube are in a range of 0.1-5 mm; and wherein a sealing member is further disposed between the first cavity and the second cavity to block a liquid return channel between the first cavity and the second cavity, and the liquid suction tube and the liquid return tube are penetrated through the sealing member.

2. The atomizer structure according to claim 1, wherein the first cavity comprises a cavity portion and a liquid return portion located below the cavity portion, the liquid return portion being in a shape of a funnel, and the opening of the third end is located at a lowermost end of the liquid return portion.

3. The atomizer structure according to claim 1, wherein the spray assembly further comprises a pressure relief hole communicating with the first cavity, and wherein the pressure relief hole allows the first cavity to communicate with an atmosphere outside the first cavity.

4. The atomizer structure according to claim 3, wherein a shape of the pressure relief hole is configured to prevent the first cavity from being separated with the atmosphere outside the first cavity when the pressure relief hole is blocked.

5. The atomizer structure according to claim 1, wherein the liquid nozzle is in a cone shape.

6. The atomizer structure according to claim 5, wherein the atomizer structure further comprises a gas supplying assembly, the gas supplying assembly comprising an air pump and an air tube connected to an outlet of the air pump, the other end of the air tube is connected with a gas nozzle, and a front end of the gas nozzle extends into the first cavity such that an opening of the gas nozzle faces an opening of the liquid nozzle.

7. The atomizer structure according to claim 5, wherein an angle of less than 90 degrees is formed between an outlet axis of the gas nozzle and an outlet axis of the liquid nozzle.

8. An atomizer comprising the atomizer structure according to claim 1 and a power supply assembly configured to supply power to the atomizer structure, and a controller electrically connected to the power supply assembly, the controller comprising a tilting switch configured to disconnect the power supply assembly from supplying power to the atomizer structure when the atomizer structure is tilted or inverted.

* * * * *